(12) United States Patent
Du et al.

(10) Patent No.: US 11,886,975 B2
(45) Date of Patent: Jan. 30, 2024

(54) METHODS AND RELATED ASPECTS FOR PATHOLOGY PROGNOSIS

(71) Applicant: THE JOHNS HOPKINS UNIVERSITY, Baltimore, MD (US)

(72) Inventors: Yong Du, Lutherville-Timonium, MD (US); Kevin H. Leung, Baltimore, MD (US); Martin Gilbert Pomper, Baltimore, MD (US)

(73) Assignee: THE JOHNS HOPKINS UNIVERSITY, Baltimore, MD (US)

( * ) Notice: Subject to any disclaimer, the term of this patent is extended or adjusted under 35 U.S.C. 154(b) by 0 days.

(21) Appl. No.: 18/253,091

(22) PCT Filed: Nov. 15, 2021

(86) PCT No.: PCT/US2021/059409
§ 371 (c)(1),
(2) Date: May 16, 2023

(87) PCT Pub. No.: WO2022/108882
PCT Pub. Date: May 27, 2022

(65) Prior Publication Data
US 2023/0342591 A1    Oct. 26, 2023

Related U.S. Application Data

(60) Provisional application No. 63/116,499, filed on Nov. 20, 2020.

(51) Int. Cl.
*G06T 7/00* (2017.01)
*G06N 3/045* (2023.01)
(Continued)

(52) U.S. Cl.
CPC ........... *G06N 3/045* (2023.01); *G06N 3/0985* (2023.01); *G06T 7/0012* (2013.01); *G06V 10/44* (2022.01);
(Continued)

(58) Field of Classification Search
CPC .... G06N 3/045; G06N 3/0985; G06T 7/0012; G06T 2207/10104; G06T 2207/10108;
(Continued)

(56) References Cited

U.S. PATENT DOCUMENTS 11,263,749 B1 * 3/2022 Purushottam .......... G16H 15/00
2005/0215889 A1 * 9/2005 Patterson, II ......... G06T 7/0012
600/436

(Continued)

FOREIGN PATENT DOCUMENTS

WO       2005094686 A2      10/2005
WO    WO-2005094686 A2 *   10/2005   ............. A61B 6/037
WO       2020047204 A1       3/2020

OTHER PUBLICATIONS

Shao, Wenyi et al. "A learned reconstruction network for SPECT imaging." IEEE transactions on radiation and plasma medical sciences 5.1 (2020): 26-34. (Year: 2020).*

(Continued)

*Primary Examiner* — Van D Huynh
(74) *Attorney, Agent, or Firm* — MH2 TECHNOLOGY LAW GROUP LLP; Christopher C. Sappenfield

(57) ABSTRACT

Provided herein are methods of generating models to predict prospective pathology scores of test subjects having a pathology in certain embodiments. Related systems and computer program products are also provided.

16 Claims, 17 Drawing Sheets

(51) Int. Cl.
*G06V 10/44* (2022.01)
*G06N 3/0985* (2023.01)

(52) U.S. Cl.
CPC .............. *G06T 2207/10104* (2013.01); *G06T 2207/10108* (2013.01); *G06T 2207/20081* (2013.01); *G06T 2207/20084* (2013.01); *G06T 2207/30016* (2013.01)

(58) Field of Classification Search
CPC . G06T 2207/20081; G06T 2207/20084; G06T 2207/30016; G06V 10/44
See application file for complete search history.

(56) References Cited

U.S. PATENT DOCUMENTS

| | | | |
|---|---|---|---|
| 2008/0101665 A1* | 5/2008 | Collins | A61B 5/4088 |
| | | | 600/407 |
| 2016/0004821 A1* | 1/2016 | Fueyo | G06F 18/22 |
| | | | 705/2 |
| 2017/0236283 A1* | 8/2017 | Lambin | A61B 5/7275 |
| | | | 382/131 |
| 2018/0068083 A1* | 3/2018 | Cohen | G16B 50/30 |
| 2021/0401392 A1* | 12/2021 | Bengtsson | A61B 6/5217 |
| 2022/0051801 A1* | 2/2022 | Feng | G06F 18/24 |
| 2022/0223231 A1* | 7/2022 | Reith | G06N 20/00 |
| 2022/0254490 A1* | 8/2022 | Addanki | G16H 50/30 |

OTHER PUBLICATIONS

Wang, X. (Authorized officer), International Preliminary Report on Patentability in corresponding International Application No. PCT/US2021/059409 dated Jun. 1, 2023, 7 pages.

Belugin, M. (Authorized officer), International Search Report and Written Opinion in corresponding International Application No. PCT/US2021/059409 dated Mar. 3, 2022, 8 pages.

Shao, Wenyi et al. "A learned reconstruction network for SPECT imaging." IEEE transactions on radiation and plasma medical sciences 5.1 (2020): 26-34.

* cited by examiner

METHODS AND RELATED ASPECTS FOR PATHOLOGY PROGNOSIS

CROSS-REFERENCE TO RELATED APPLICATIONS

This application is the national stage entry of International Patent Application No. PCT/US2021/059409, filed on Nov. 15, 2021, and published as WO 2022/108882 A1 on May 27, 2022, which claims the benefit of U.S. Provisional Patent Application Ser. No. 63/116,499, filed Nov. 20, 2020, both of which are hereby incorporated by reference herein in their entireties.

STATEMENT OF GOVERNMENT SUPPORT

This invention was made using U.S. Government support under grant NS094227 awarded by the National Institutes of Health. The U.S. Government has certain rights in this invention.

BACKGROUND

Accurate prediction of outcome in patients with pathologies, such as Parkinson's disease (PD) is important for the development of treatments for those pathologies. Medical imaging techniques like single photon emission tomography (SPECT) and positron emission tomography (PET) imaging has become increasingly used to inform the diagnosis of PD, among other pathologies. For example, in vivo imaging of dopamine transporter, a transmembrane protein that reuptakes dopamine from the synaptic cleft, with SPECT and/or PET may be useful for monitoring disease progression of patients with pathologies, such as PD. Some examples of compounds that can be radiolabed for dopamine transporter-targeted SPECT and/or PET imaging include, but are not limited to, IPT, β-CIT, FP-CIT, and β-CFT. However, accurate prediction of outcome in, for example, PD is challenging due to the high variability of the clinical measures used to monitor progression motor symptoms. Accordingly, there is a need for additional methods, and related aspects, for prognosticating various pathologies, including PD and other neurological disorders.

SUMMARY

The present disclosure relates, in certain aspects, to methods, systems, and computer readable media of use in generating models to predict prospective pathology scores of test subjects having a given pathology and predicting patient outcomes using those models. The methods and other aspects of the present disclosure are also adapted for use in the early detection of pathologies in subjects having pathologies with rapid rates of progression and which have high pathology scores over a relatively short duration. In some exemplary embodiments, the methods and other aspects are implemented as prognostic tools that are used to further characterize subjects with a given pathology into stages of that pathology. These and other aspects will be apparent upon a complete review of the present disclosure, including the accompanying figures.

In one aspect, the present disclosure provides method of generating a model to predict prospective pathology scores of test subjects having a pathology, to detect pathologies having rapid rates of progression in the test subjects, and/or to stage the pathologies in the test subjects. The method includes extracting a plurality of image features from sets of longitudinal single photon emission computed tomography (SPECT) and/or positron emission tomography (PET) images obtained from a plurality of reference subjects having the pathology to produce at least one image feature vector. The method also includes extracting a plurality of non-imaging features from non-imaging data obtained from the plurality of reference subjects having the pathology to produce at least one non-imaging feature vector. In addition, the method also includes training multiple artificial neural networks (ANNs) using the image feature vector and the non-imaging vector to produce an ensemble of ANNs, thereby generating the model to predict prospective pathology scores of test subjects having the pathology, to detect pathologies having rapid rates of progression in the test subjects, and/or to stage the pathologies in the test subjects.

In another aspect, the present disclosure provides a method of generating a model to predict prospective pathology scores of test subjects having a pathology. The method includes extracting a first plurality of image features directly from sets of longitudinal single photon emission computed tomography (SPECT) and/or positron emission tomography (PET) images obtained from a plurality of reference subjects having the pathology in which the image features extracted from at least first and second sets of the longitudinal SPECT and/or PET images are extracted separate from one another to produce a first feature vector. The method also includes extracting a second plurality of image features from maximum intensity projections (MIPs) of the sets of the longitudinal SPECT and/or PET images to produce a second feature vector, extracting a third plurality of image features from semi-quantitative imaging measures of the sets of the longitudinal SPECT and/or PET images to produce a third feature vector, and extracting a plurality of non-imaging features from non-imaging data obtained from the plurality of reference subjects having the pathology to produce a fourth feature vector. In addition, the method also includes training multiple artificial neural networks (ANNs) using the first, second, third, and fourth feature vectors and a plurality of clinical features from clinical data obtained from the plurality of reference subjects having the pathology to produce an ensemble of ANNs, thereby generating the model to predict prospective pathology scores of test subjects having the pathology.

In another aspect, the present disclosure provides a method of generating a model to predict prospective pathology scores of test subjects having a pathology. The method includes extracting a first plurality of image features from sets of longitudinal single photon emission computed tomography (SPECT) and/or positron emission tomography (PET) images obtained from a plurality of reference subjects having the pathology in which the images features extracted from at least first and second sets of the longitudinal SPECT and/or PET images are extracted separate from one another to produce a first feature vector. The method also includes extracting a second plurality of image features from the sets of the longitudinal SPECT and/or PET images when the longitudinal SPECT and/or PET images are in an unprocessed form to produce a second feature vector, and extracting a plurality of clinical features from clinical data obtained from the plurality of reference subjects having the pathology, which clinical features comprise pathology sub-scores to produce a third feature vector. In addition, the method also includes training one or more layers of an artificial neural network (ANN) using the first, second, and third feature vectors, thereby generating the model to predict prospective pathology scores of test subjects having the pathology.

In some embodiments, the methods disclosed herein further include training at least one of the layers of the ANN using one or more conventional imaging features obtained from the longitudinal SPECT and/or PET images. In some embodiments, the methods disclosed herein further include predicting a prospective pathology score of a test subject having the pathology using the model.

In some embodiments, the ensemble of ANNs comprises at least one convolutional neural network (CNN) and at least one recurrent neural network (RNN). In some embodiments, the SPECT and/or PET images comprise dopamine transporter SPECT (DatSPECT) and/or PET images. Herein, DatSPECT refers to the use of radiotracers that target dopamine transporter in SPECT imaging. In some embodiments, the SPECT images comprise raw or unprocessed SPECT and/or raw or unprocessed PET images.

In some embodiments, the methods disclosed herein include extracting one or more of the plurality of image features using at least one artificial neural network (ANN). In some embodiments, the ANN is not further trained on a classification task. In some embodiments, the ANN comprises one or more recurrent neural networks (RNNs). In some of these embodiments, the RNNs comprise one or more long short-term memory (LSTM) networks and/or one or more gated recurrent units (GRUs). In some embodiments, the methods disclosed herein include extracting the second plurality of image features using one or more pre-trained convolutional neural networks (CNNs).

In some embodiments, the semi-quantitative imaging measures are of striatal binding ratios and/or other radiomic features of the sets of the longitudinal SPECT and/or PET images. In some embodiments, the non-imaging features comprise pathology sub-scores, patient histories, medical records, patient demographic information, genomic data, proteomic data, and/or the like. In some embodiments, the pathology sub-scores comprise unified Parkinson's disease rating scale (UPDRS) sub-scores (e.g., UPDRS-III scores, etc.).

In some embodiments, the pathology comprises a type of dementia and/or brain disorder. In some embodiments, the type of dementia is selected from the group consisting of: Parkinson's disease (PD), Alzheimer's disease (AD), Lewy Body Dementia (LBD), Creutzfeldt-Jakob disease (CJD), frontotemporal dementia (FTD), Huntington's disease (HD), normal pressure hydrocephalus (NPH), posterior cortical atrophy (PCA), vascular dementia, and Korsakoff syndrome. In some embodiments, the type of brain disorder is selected from the group consisting of: schizophrenia and epilepsy.

In another aspect, the present disclosure provides a system, comprising at least one controller that comprises, or is capable of accessing, computer readable media comprising non-transitory computer executable instructions which, when executed by at least one electronic processor, perform at least: extracting a plurality of image features from sets of longitudinal single photon emission computed tomography (SPECT) and/or positron emission tomography (PET) images obtained from a plurality of reference subjects having the pathology to produce at least one image feature vector; extracting a plurality of non-imaging features from non-imaging data obtained from the plurality of reference subjects having the pathology to produce at least one non-imaging feature vector; training multiple artificial neural networks (ANNs) using the image feature vector and the non-imaging vector to produce an ensemble of ANNs; and using the ensemble of ANNs to predict a prospective pathology score of a test subject having the pathology, to detect pathologies having rapid rates of progression in the test subjects, and/or to stage the pathologies in the test subjects.

In another aspect, the present disclosure provides a system, comprising at least one controller that comprises, or is capable of accessing, computer readable media comprising non-transitory computer executable instructions which, when executed by at least one electronic processor, perform at least: extracting a first plurality of image features directly from sets of longitudinal single photon emission computed tomography (SPECT) and/or positron emission tomography (PET) images obtained from a plurality of reference subjects having the pathology, wherein the images features extracted from at least first and second sets of the longitudinal SPECT and/or PET images are extracted separate from one another to produce a first feature vector; extracting a second plurality of image features from maximum intensity projections (MIPs) of the sets of the longitudinal SPECT and/or PET images to produce a second feature vector; extracting a third plurality of image features from semi-quantitative imaging measures of the sets of the longitudinal SPECT and/or PET images to produce a third feature vector; extracting a plurality of non-imaging features from non-imaging data obtained from the plurality of reference subjects having the pathology to produce a fourth feature vector; training multiple artificial neural networks (ANNs) using the first, second, third, and fourth feature vectors and a plurality of clinical features from clinical data obtained from the plurality of reference subjects having the pathology to produce an ensemble of ANNs; and using the ensemble of ANNs to predict a prospective pathology score of a test subject having the pathology.

In another aspect, the present disclosure provides a system, comprising at least one controller that comprises, or is capable of accessing, computer readable media comprising non-transitory computer executable instructions which, when executed by at least one electronic processor, perform at least: extracting a first plurality of image features from sets of longitudinal single photon emission computed tomography (SPECT) and/or positron emission tomography (PET) images obtained from a plurality of reference subjects having the pathology, wherein the image features extracted from at least first and second sets of the longitudinal SPECT and/or PET images are extracted separate from one another to produce a first feature vector; extracting a second plurality of image features from the sets of the longitudinal SPECT images when the longitudinal SPECT and/or PET images are in an unprocessed form to produce a second feature vector; extracting a plurality of clinical features from clinical data obtained from the plurality of reference subjects having the pathology, which clinical features comprise pathology sub-scores to produce a third feature vector; training one or more layers of an artificial neural network (ANN) using the first, second, and third feature vectors to generate a predictive model; and using the predictive model to predict a prospective pathology score of a test subject having the pathology.

In another aspect, the present disclosure provides a computer readable media comprising non-transitory computer executable instruction which, when executed by at least one electronic processor perform at least: extracting a plurality of image features from sets of longitudinal single photon emission computed tomography (SPECT) and/or positron emission tomography (PET) images obtained from a plurality of reference subjects having the pathology to produce at least one image feature vector; extracting a plurality of non-imaging features from non-imaging data obtained from the plurality of reference subjects having the pathology to produce at least one non-imaging feature vector; training multiple artificial neural networks (ANNs) using the image feature vector and the non-imaging vector to produce an ensemble of ANNs; and using the ensemble of ANNs to predict a prospective pathology score of a test subject having the pathology.

In another aspect, the present disclosure provides a computer readable media comprising non-transitory computer executable instruction which, when executed by at least one electronic processor perform at least: extracting a first plurality of image features directly from sets of longitudinal single photon emission computed tomography (SPECT) and/or positron emission tomography (PET) images obtained from a plurality of reference subjects having the pathology, wherein the image features extracted from at least first and second sets of the longitudinal SPECT and/or PET images are extracted separate from one another to produce a first feature vector; extracting a second plurality of image features from maximum intensity projections (MIPs) of the sets of the longitudinal SPECT and/or PET images to produce a second feature vector; extracting a third plurality of image features from semi-quantitative imaging measures of the sets of the longitudinal SPECT and/or PET images to produce a third feature vector; extracting a plurality of non-imaging features from non-imaging data obtained from the plurality of reference subjects having the pathology to produce a fourth feature vector; training multiple artificial neural networks (ANNs) using the first, second, third, and fourth feature vectors and a plurality of clinical features from clinical data obtained from the plurality of reference subjects having the pathology to produce an ensemble of ANNs; and using the ensemble of ANNs to predict a prospective pathology score of a test subject having the pathology.

In another aspect, the present disclosure provides a computer readable media comprising non-transitory computer executable instruction which, when executed by at least electronic processor perform at least: extracting a first plurality of image features from sets of longitudinal single photon emission computed tomography (SPECT) and/or positron emission tomography (PET) images obtained from a plurality of reference subjects having the pathology, wherein the image features extracted from at least first and second sets of the longitudinal SPECT and/or PET images are extracted separate from one another to produce a first feature vector; extracting a second plurality of image features from the sets of the longitudinal SPECT and/or PET images when the longitudinal SPECT and/or PET images are in an unprocessed form to produce a second feature vector; extracting a plurality of clinical features from clinical data obtained from the plurality of reference subjects having the pathology, which clinical features comprise pathology sub-scores to produce a third feature vector; training one or more layers of an artificial neural network (ANN) using the first, second, and third feature vectors to generate a predictive model; and using the predictive model to predict a prospective pathology score of a test subject having the pathology.

BRIEF DESCRIPTION OF THE DRAWINGS

The accompanying drawings, which are incorporated in and constitute a part of this specification, illustrate certain embodiments, and together with the written description, serve to explain certain principles of the methods, systems, and related computer readable media disclosed herein. The description provided herein is better understood when read in conjunction with the accompanying drawings which are included by way of example and not by way of limitation.

It will be understood that like reference numerals identify like components throughout the drawings, unless the context indicates otherwise. It will also be understood that some or all of the figures may be schematic representations for purposes of illustration and do not necessarily depict the actual relative sizes or locations of the elements shown.

DEFINITIONS

Figure 1:
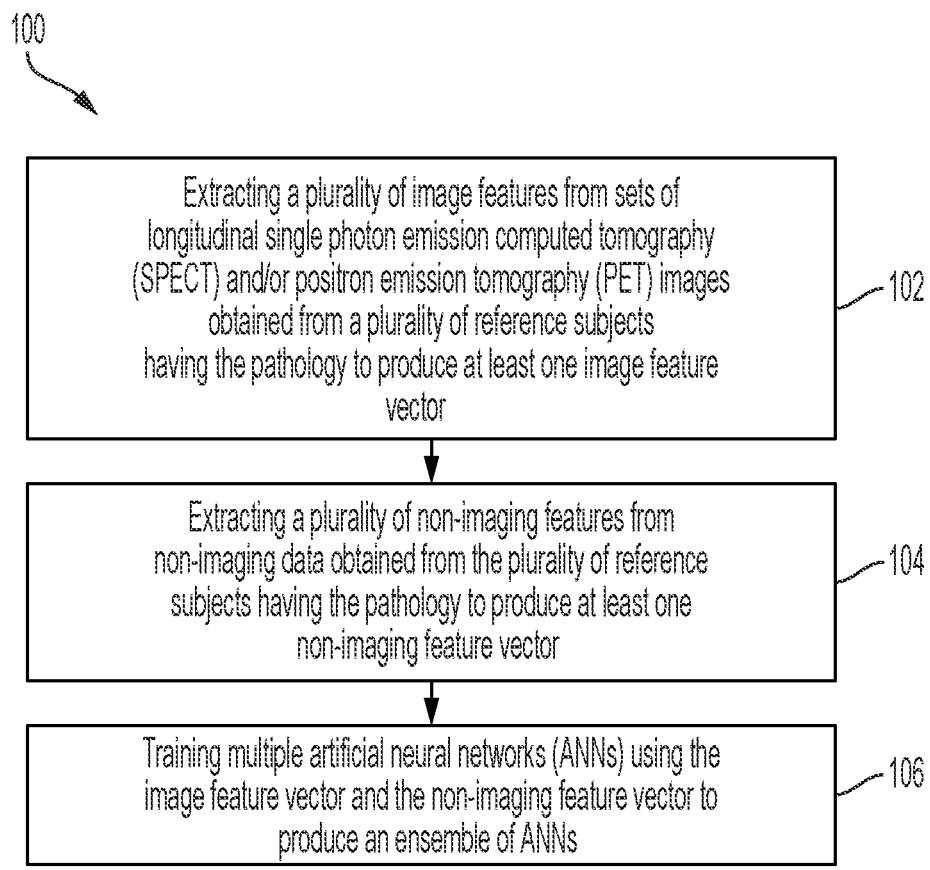
FIG. 1 is a flow chart that schematically depicts exemplary method steps according to some aspects disclosed herein.

In order for the present disclosure to be more readily understood, certain terms are first defined below. Additional definitions for the following terms and other terms may be set forth through the specification. If a definition of a term set forth below is inconsistent with a definition in an application or patent that is incorporated by reference, the definition set forth in this application should be used to understand the meaning of the term.

As used in this specification and the appended claims, the singular forms "a," "an," and "the" include plural references unless the context clearly dictates otherwise. Thus, for example, a reference to "a method" includes one or more methods, and/or steps of the type described herein and/or which will become apparent to those persons skilled in the art upon reading this disclosure and so forth.

It is also to be understood that the terminology used herein is for the purpose of describing particular embodiments only and is not intended to be limiting. Further, unless defined otherwise, all technical and scientific terms used herein have the same meaning as commonly understood by one of ordinary skill in the art to which this disclosure pertains. In describing and claiming the methods, computer readable media, systems, and component parts, the following terminology, and grammatical variants thereof, will be used in accordance with the definitions set forth below.

About: As used herein, "about" or "approximately" or "substantially" as applied to one or more values or elements of interest, refers to a value or element that is similar to a stated reference value or element. In certain embodiments, the term "about" or "approximately" or "substantially" refers to a range of values or elements that falls within 25%, 20%, 19%, 18%, 17%, 16%, 15%, 14%, 13%, 12%, 11%, 10%, 9%, 8%, 7%, 6%, 5%, 4%, 3%, 2%, 1%, or less in either direction (greater than or less than) of the stated reference value or element unless otherwise stated or otherwise evident from the context (except where such number would exceed 100% of a possible value or element).

Machine Learning Algorithm: As used herein, "machine learning algorithm" generally refers to an algorithm, executed by computer, that automates analytical model building, e.g., for clustering, classification or pattern recognition. Machine learning algorithms may be supervised or unsupervised. Learning algorithms include, for example, artificial neural networks (e.g., back propagation networks), discriminant analyses (e.g., Bayesian classifier or Fisher's analysis), support vector machines, decision trees (e.g., recursive partitioning processes such as CART—classification and regression trees, or random forests), linear classifiers (e.g., multiple linear regression (MLR), partial least squares (PLS) regression, and principal components regression), hierarchical clustering, and cluster analysis. A dataset on which a machine learning algorithm learns can be referred to as "training data." A model produced using a machine learning algorithm is generally referred to herein as a "machine learning model."

Pathology: As used herein, "pathology" refers to a deviation from a normal state of health, such as a disease (e.g., neoplastic or non-neoplastic diseases), abnormal condition, or disorder.

Reference Subjects: As used herein, "reference subjects" refers to a set of subjects having or known to have or lack specific properties (e.g., known pathologies in associated subjects and/or the like) that is used to generate pathology models (e.g., as training data) and/or analyzed along with or compared to test subjects in order to evaluate the accuracy of an analytical procedure. A set of reference subjects typically includes from at least about 25 to at least about 10,000,000 or more reference subjects. In some embodiments, a set of reference subjects includes about 50, 75, 100, 150, 200, 300, 400, 500, 600, 700, 800, 900, 1,000, 2,500, 5,000, 7,500, 10,000, 15,000, 20,000, 25,000, 50,000, 100,000, 1,000,000, or more reference subjects.

Subject: As used herein, "subject" or "test subject" refers to an animal, such as a mammalian species (e.g., human) or avian (e.g., bird) species. More specifically, a subject can be a vertebrate, e.g., a mammal such as a mouse, a primate, a simian or a human. Animals include farm animals (e.g., production cattle, dairy cattle, poultry, horses, pigs, and the like), sport animals, and companion animals (e.g., pets or support animals). A subject can be a healthy individual, an individual that has or is suspected of having a disease or pathology or a predisposition to the disease or pathology, or an individual that is in need of therapy or suspected of needing therapy. The terms "individual" or "patient" are intended to be interchangeable with "subject." A "reference subject" refers to a subject known to have or lack specific properties (e.g., known ocular or other pathology and/or the like).

DETAILED DESCRIPTION

There exists an important need for the discovery of definitive biomarkers for Parkinson's disease (PD), among other pathologies. Accurate prediction of outcome in patients with PD is important for the development of treatments for PD. Dopamine transporter single photon emission tomography (DatSPECT) imaging has become increasingly used to inform the diagnosis of PD. However, accurate prediction of outcome in PD is challenging due to the high variability of the clinical measures used to monitor progression motor symptoms. To address this need, the present disclosure provides, in certain embodiments, a three-stage convolutional recurrent neural network (CNN-RNN) ensemble-based deep learning approach to predict longitudinal motor outcome in patients with PD and/or another pathology. In some embodiments, the first stage extracts relevant DatSPECT imaging features from years 0 (baseline) and 1, or another longitudinal timeframe, using a CNN-RNN-based network architecture. As described further herein, several different methods for DatSPECT image feature extraction are optionally used in this stage. For example, commonly used CNN-based architectures pretrained on the ImageNet dataset, including VGG16, ResNet50, DenseNet121, and InceptionV3, are used as DatSPECT image feature extractors in certain embodiments. In some embodiments, features are also extracted from semi-quantitative imaging measures of striatal binding ratios in the left and right caudate and putamen in DatSPECT images. In some embodiments, the second stage extracts relevant features from clinical measures of motor symptoms from, for example, years 0 and 1 using an RNN-based architecture. In some embodiments, the third stage trains an ensemble learning-based approach to train multiple neural networks on different subsets of the extracted features. In some embodiments, predictions from all networks are combined in an unweighted average to yield the final predicted motor outcome of patients with PD in, for example, year 4 or another timepoint. These and other aspects will be apparent upon a complete review of the present disclosure, including the accompanying example and figures.

To illustrate, FIG. 1 is a flow chart that schematically depicts exemplary method steps of generating a model to predict prospective pathology scores of test subjects having a pathology. As shown, method 100 includes extracting a plurality of image features from sets of longitudinal single photon emission computed tomography (SPECT) and/or positron emission tomography (PET) images obtained from a plurality of reference subjects having the pathology (e.g., Parkinson's disease, etc.) to produce at least one image feature vector (step 102). Method 100 also includes extracting a plurality of non-imaging features from non-imaging data obtained from the plurality of reference subjects having the pathology to produce at least one non-imaging feature vector (step 104). In addition, method 100 also includes training multiple artificial neural networks (ANNs) using the image feature vector and the non-imaging feature vector to produce an ensemble of ANNs to generate the model to predict prospective pathology scores of test subjects having the pathology (step 106).

Figure 2:
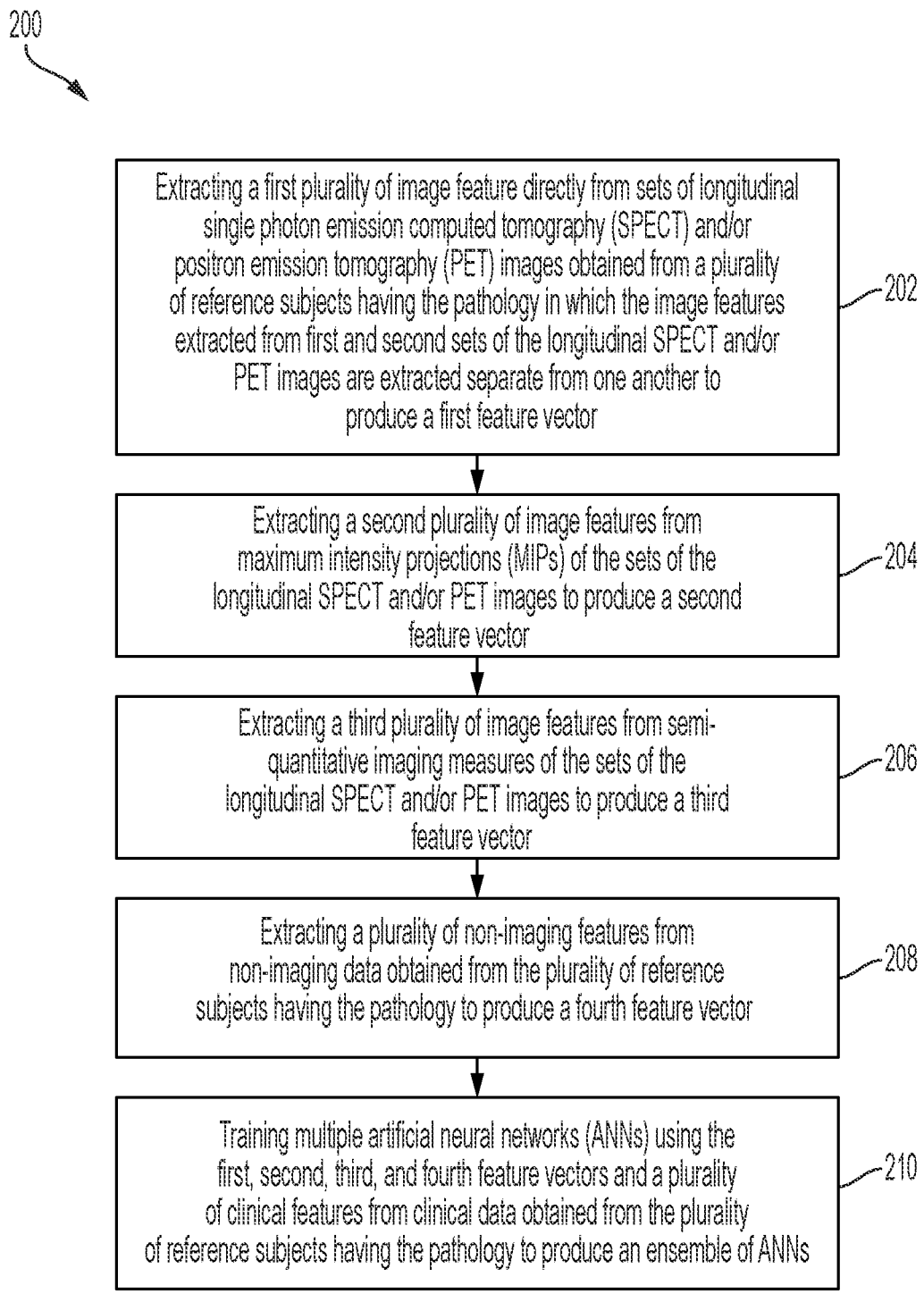
FIG. 2 is a flow chart that schematically depicts exemplary method steps according to some aspects disclosed herein.

To further illustrate, FIG. 2 is a flow chart that schematically depicts some exemplary method steps of generating a model to predict prospective pathology scores of test subjects having a pathology. As shown, method 200 includes extracting a first plurality of image features directly from sets of longitudinal single photon emission computed tomography (SPECT) and/or positron emission tomography (PET) images obtained from a plurality of reference subjects having the pathology in which the image features extracted from at least first and second sets of the longitudinal SPECT and/or PET images are extracted separate from one another to produce a first feature vector (step 202). Method 200 also includes extracting a second plurality of image features from maximum intensity projections (MIPs) of the sets of the longitudinal SPECT and/or PET images to produce a second feature vector (step 204), extracting a third plurality of image features from semi-quantitative imaging measures of the sets of the longitudinal SPECT and/or PET images to produce a third feature vector (step 206), and extracting a plurality of non-imaging features from non-imaging data obtained from the plurality of reference subjects having the pathology to produce a fourth feature vector (step 208). In addition, method 200 also includes training multiple artificial neural networks (ANNs) using the first, second, third, and fourth feature vectors and a plurality of clinical features from clinical data obtained from the plurality of reference subjects having the pathology to produce an ensemble of ANNs to generate the model to predict prospective pathology scores of test subjects having the pathology (step 210).

Figure 3:
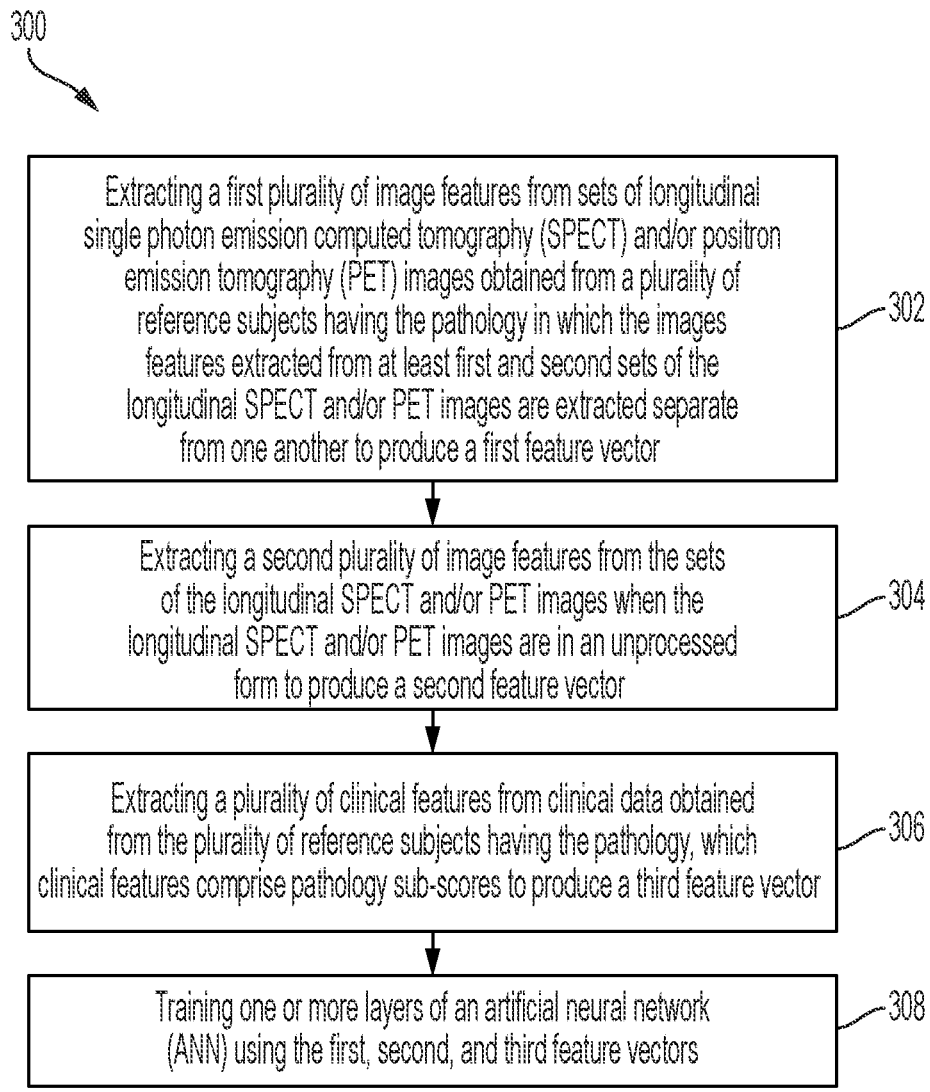
FIG. 3 is a flow chart that schematically depicts exemplary method steps according to some aspects disclosed herein.

To further illustrate, FIG. 3 is a flow chart that schematically depicts some exemplary method steps of generating a model to predict prospective pathology scores of test subjects having a pathology. As shown, method 300 includes extracting a first plurality of image features from sets of longitudinal single photon emission computed tomography (SPECT) and/or positron emission tomography (PET) images obtained from a plurality of reference subjects having the pathology in which the images features extracted from at least first and second sets of the longitudinal SPECT and/or PET images are extracted separate from one another to produce a first feature vector (step 302). Method 300 also includes extracting a second plurality of image features from the sets of the longitudinal SPECT and/or PET images when the longitudinal SPECT and/or PET images are in an unprocessed or raw form to produce a second feature vector (step 304), and extracting a plurality of clinical features from clinical data obtained from the plurality of reference subjects having the pathology, which clinical features comprise pathology sub-scores to produce a third feature vector (step 306). In addition, method 300 also includes training one or more layers of an artificial neural network (e.g., one or more recurrent neural networks (RNNs), such as one or more long short-term memory (LSTM) networks, one or more gated recurrent units (GRUs), and/or the like) using the first, second, and third feature vectors to generate the model to predict prospective pathology scores of test subjects having the pathology (step 308).

In some embodiments, the methods disclosed herein further include training at least one of the layers of the ANN using one or more conventional imaging features obtained from the longitudinal SPECT and/or PET images. In some embodiments, the methods disclosed herein further include predicting a prospective pathology score of a test subject having the pathology using the model. In some embodiments, the ensemble of ANNs comprises at least one convolutional neural network (CNN) and at least one recurrent neural network (RNN). In some embodiments, the SPECT and/or PET images comprise dopamine transporter SPECT (DatSPECT) and/or PET images. Herein, DatSPECT refers to the use of radiotracers that target dopamine transporter in SPECT imaging. In some embodiments, the SPECT images comprise raw or unprocessed SPECT and/or raw or unprocessed PET images.

In some embodiments, the methods disclosed herein include extracting one or more of the plurality of images features using at least one artificial neural network (ANN). In some embodiments, the ANN is not further trained on a classification task. In some embodiments, the ANN comprises one or more recurrent neural networks (RNNs). In some of these embodiments, the RNNs comprise one or more long short-term memory (LSTM) networks and/or one or more gated recurrent units (GRUs). In some embodiments, the methods disclosed herein include extracting the second plurality of images features using one or more pre-trained convolutional neural networks (CNNs).

In some embodiments, the semi-quantitative imaging measures are of striatal binding ratios and/or other radiomic features of the sets of the longitudinal SPECT and/or PET images. In some embodiments, the non-imaging features comprise pathology sub-scores, patient histories, medical records, patient demographic information, genomic data, proteomic data, and/or the like. In some embodiments, the pathology sub-scores comprise unified Parkinson's disease rating scale (UPDRS) sub-scores (e.g., UPDRS-III scores, etc.).

In some embodiments, the pathology comprises a type of dementia and/or brain disorder. In some embodiments, the type of dementia is selected from the group consisting of: Parkinson's disease (PD), Alzheimer's disease (AD), Lewy Body Dementia (LBD), Creutzfeldt-Jakob disease (CJD), frontotemporal dementia (FTD), Huntington's disease (HD), normal pressure hydrocephalus (NPH), posterior cortical atrophy (PCA), vascular dementia, and Korsakoff syndrome. In some embodiments, the type of brain disorder is selected from the group consisting of: schizophrenia and epilepsy.

EXAMPLE: A THREE-STAGE CONVOLUTIONAL RECURRENT NEURAL NETWORK ENSEMBLE-BASED DEEP LEARNING APPROACH TO PREDICT LONGITUDINAL OUTCOME OF PATIENTS WITH PARKINSON'S DISEASE

1. Introduction

Parkinson's disease (PD) is one of the most common neurodegenerative disorder that is characterized by loss of dopaminergic neurons in the substantia nigra. The loss of striatal dopaminergic neurons can cause the presence of progressive motor and nonmotor symptoms. Motor symptoms can include bradykinesia, resting tremor, muscular rigidity, and postural instability. Nonmotor symptoms include cognitive problems and autonomic nervous system dysfunction that can occur at late stages of PD.

The Unified Parkinson's Disease Rating Scale (UPDRS) is the most commonly used scale for assessing the clinical status of PD patients. The UPDRS is a four part tool that assesses both motor and nonmotor symptoms of patients with PD. An increase of 2.5 points on part III of the UPDRS (UPDRS-III) motor assessment score has been shown to be a clinically important difference for determining meaningful changes in PD progression.

The diagnosis of PD is informed by the presence of key motor and nonmotor symptoms and by imaging the dopamine system with dopamine transporter single photon emission computed tomography (DatSPECT) (de la Fuente-Fernandez 2012). There is an important need for identifying biomarkers for PD progression and prediction of outcome in PD to power clinical studies. For this purpose, the Parkinson's Progression Markers Initiative (PPMI) made available longitudinal clinical data that included a database of DatSPECT images and clinical measures. In this Example, [$^{123}$I]ioflupane is the specific radiotracer used for DatSPECT imaging.

Several studies have developed predictive methods for PD based on traditional machine learning techniques using data from PPMI. One study used support vector machine (SVM) and logistic regression analysis to detect patients with early PD based on SBR values extracted from PPMI data. Another method used clinical measures, DatSPECT imaging, and cerebrospinal fluid biomarkers from PPMI as inputs to a logistic regression algorithm for diagnosis of cognitive impairment. Another study used SBR values from PPMI and compared the performance of several traditional machine learning methods on the task of detecting the presence of early PD. A random forest analysis utilizing radiomic features extracted from DatSPECT images improved prediction of motor outcome in patients with PD. A SVM-based method improved classification between patients with PD and healthy controls based on SBR values and circularity shape features from DatSPECT scans.

Deep learning methods have recently shown promise for medical image analysis and disease detection tasks. In particular, deep learning methods based on convolutional neural networks (CNNs) have had success in disease classification tasks on medical images while those based on recurrent neural networks (RNNs) have had similar success in time series prediction. Additionally, ensemble learning methods have also been developed to improve the accuracy of prediction tasks by combining multiple classifier systems to reduce the variance of prediction.

Figure 4:
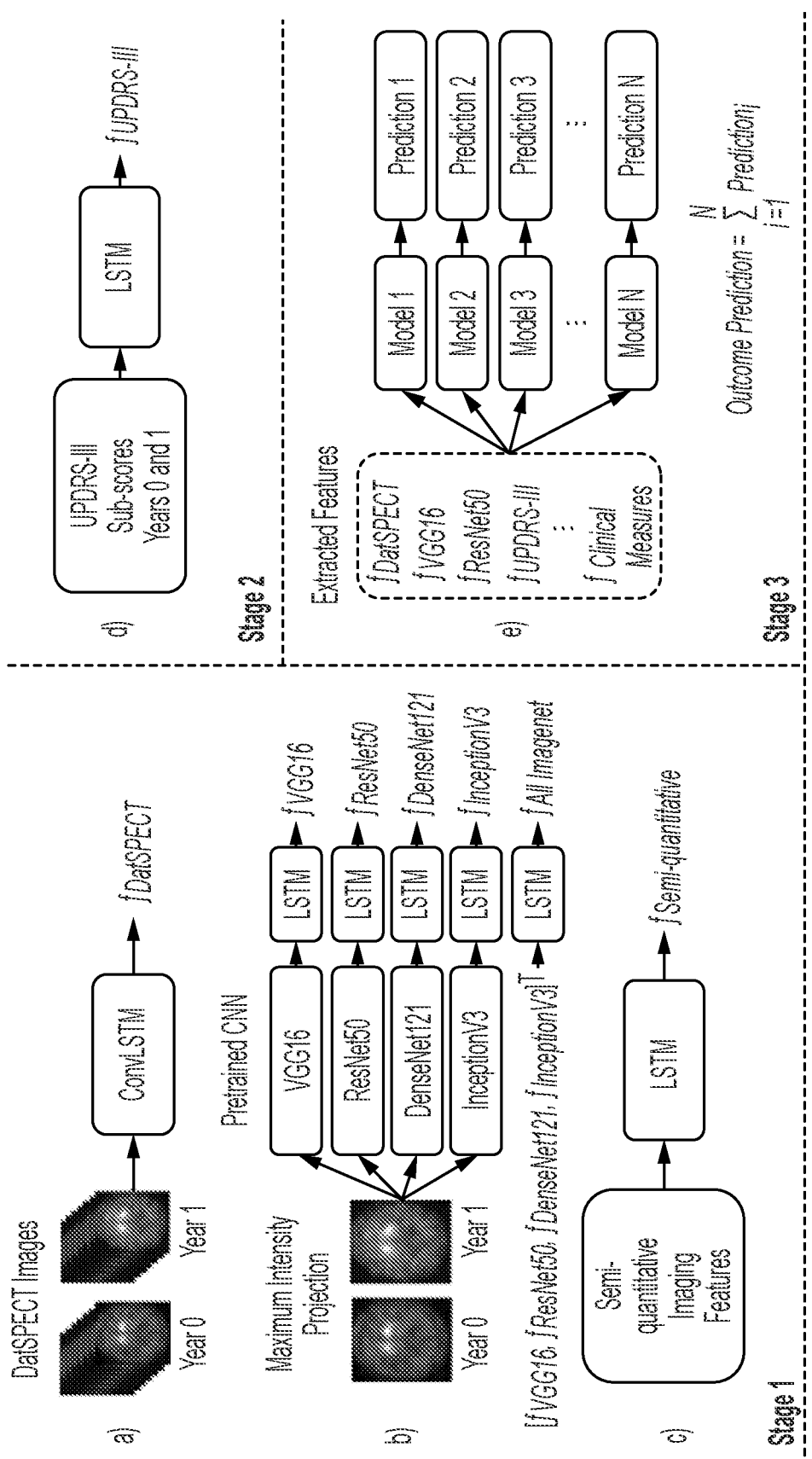
FIG. 4 (panels a-e) is an illustration of a three-stage ensemble-based deep learning approach according to an exemplary embodiment. The DatSPECT image feature extraction methods in Stage 1 using the procedures in Example Section 2.2.1 are shown in (a-c). The UPDRS-III feature extraction method in Stage 2 using the procedure in Example Section 2.2.2 are shown in (d). The feature aggregation and ensemble-based prediction in Stage 3 using the procedure in Example Section 2.2.3 is shown in (e).

Thus, the objective in this study was to develop a three-stage convolutional neural network (CNN)-recurrent neural network (RNN) ensemble-based deep learning approach to predict longitudinal motor outcome of patients with PD (FIG. 4). The approach was developed in the context of predicting motor UPDRS-III scores in year 4 by incorporating both imaging and non-imaging clinical measures from year 0 (baseline) and year 1. The first stage of approach extracted relevant spatiotemporal features directly from DatSPECT imaging using a CNN-RNN-based network architecture (FIG. 4a-c). The second stage extracted the relevant clinical temporal features from UPDRS-III motor scores using an RNN-based architecture (FIG. 4d). The third stage employed an ensemble learning approach that combined those extracted features with other clinical measures to predict motor outcome of patients with PD in year 4 (FIG. 4e). The ensemble-based deep learning approach showed significant promise for longitudinal motor outcome prediction of patients with PD, provided multiple methods for extracting the relevant features from DatSPECT images and non-imaging clinical measures, and demonstrated the importance of combining imaging and clinical measures for the outcome prediction task.

2. Methods and Materials

Retrospective data from the publically available PPMI database were used in this study. DatSPECT images and clinical measures from 198 patients with PD (144 males and 54 females, mean age 67.6±10.0 [standard deviation] years, age range 39-91) were extracted from the PPMI database. Striatal binding ratio (SBR) values in the left and right caudate nuclei and putamina of DatSPECT images were extracted and are referred to as semi-quantitative imaging features in this Example. SBR is defined as the ratio of specific uptake in the striatum to non-specific binding in the background. UPDRS-III sub-scores relating to motor signs of PD were extracted. Other clinical measures included age, gender, and diagnosis duration with respect to time of diagnosis and time of appearance of symptoms. DatSPECT images, UPDRS-III information and other clinical measures from year 0 (baseline) and year 1 were used as predictors. The composite of the UPDRS-III sub-scores in year 4 (mean score 30.7±10.5 [standard deviation], range 9.3-77.0) was used as outcome for the prediction task where a higher score indicates higher severity of motor symptoms.

2.1 Data Processing

The DatSPECT images from years 0 and 1 were preprocessed by selecting a continuous segment of 22 transaxial image slices of each image volume where the central slice had the highest relative mean uptake intensity. This was done to capture the complete structure of the striatum and to remove image slices of relatively lower intensity and higher noise. The DatSPECT images had a cubic voxel size of 2 mm. The images were zero padded resulting in an image size of 128×128.

A time series of thirty-three measured UPDRS-III sub-scores relating to motor signs of PD were extracted at the timepoints of screening, baseline, 3, 6, 9, 12, 42, 48 and 54 months. Those sub-scores reflected the motor signs of PD, including speech, facial expression, rigidity, finger tapping, hand movements, pronation supination movements of hands, toe tapping, leg agility, arising from chair, gait, freezing of gait, postural stability, posture, body bradykinesia, postural and kinetic tremor of the hands, rest tremor amplitude, constancy of rest tremor. Information about whether the patient was receiving medication for treating symptoms of PD and the clinical state patients receiving medication (good or poor response) at each timepoint were also extracted. The observed UPDRS-III sub-scores, composite score and treatment information from years 0 to 1 (screening, baseline, 3, 6, 9, and 12 months) were used as inputs to the approach. The composite UPDRS-III score or the sum of all sub-scores at those timepoints for years 0 and 1 was also used as an input to the network. This resulted in an input time sequence consisting of six time points with thirty-six features that we referred to as the input UPDRS-III information. The UPDRS-III sub-scores at 42, 48 and 54 months were summed and averaged to yield the composite UPDRS-III scores at year 4 which were used as outcome. The outcome prediction was formulated as a regression task as the composite UPDRS-III score at year 4 is a continuous value.

The clinical data were randomly partitioned into training, validation and test sets using an 60%/20%/20% split, where the training, validation and test sets consisted of 118, 40 and 40 patients, respectively. The training and validation sets were used to optimize the hyperparameters of the proposed approach. The test set was used only to evaluate the final network architecture.

2.2 Three-Stage CNN-RNN Deep Learning Ensemble-Based Approach

The three-stage CNN-RNN deep learning ensemble-based approach is illustrated in FIG. 4. The three stages consisted of (1) extraction of DatSPECT imaging features from years 0 and 1, (2) extraction of UPDRS-III sub-scores from years 0 and 1, and (3) an ensemble learning-based approach to prediction of the composite UPDRS-III scores in year 4 using the combined extracted features and other clinical measures as inputs. Each stage is discussed in detail below.

2.2.1 Stage 1: DatSPECT Image Feature Extraction

In the first stage of the approach, relevant imaging features for the prediction task were extracted from DatSPECT images in years 0 and 1. Feature extraction was performed using three different methods. In the first method, features were extracted from the original DatSPECT images from years 0 and 1 using a convolutional long short-term memory (LSTM)-based network architecture (FIG. 4a). LSTM networks are a variant of RNNs. In the second method, features were extracted from the maximum intensity projections (MIPs) of the DatSPECT images from years 0 and 1 using four commonly used convolutional neural network (CNN) architectures that were pre-trained on the ImageNet dataset of natural images (FIG. 4b). In the third method, features were extracted from semi-quantitative imaging measures from years 0 and 1 using a LSTM-based network architecture (FIG. 4c). These methods for image feature extraction are further described below.

2.2.1.1 Image Feature Extraction with a Convolutional LSTM-Based Network Architecture The DatSPECT images from years 0 and 1 were input as a time sequence, containing two time points at years 0 and 1, into a convolutional LSTM-based network architecture for feature extraction (FIG. 4a). The convolutional LSTM network is a type of recurrent neural network architecture that is similar to a LSTM-based architecture where the input and recurrent transformations are both convolutional. The convolutional LSTM-based networks have been shown to be able to better capture spatiotemporal correlations in the input data where the input data is spatiotemporal sequences.

The DatSPECT image volumes from years 0 and 1 used as inputs consisted of 22 consecutive transaxial slices that contained the complete structure of the straitum. The output of the convolutional LSTM layer was then input into a batch normalization layer followed by three dimensional (3D) convolutional layer and 3D global average pooling layers. Batch normalization has been shown to stabilize of learning and accelerate training by normalizing each batch of inputs into subsequent layers of the network. The output of the global average pooling layer was an N-dimensional extracted feature vector containing information about the original input DatSPECT images from years 0 and 1 relevant for the prediction task. Here, the dimensionality of the extracted feature vector was N=64.

2.2.1.2 Image Feature Extraction with Pretrained CNNs

Deep learning methods typically require very large training data sizes, on the order of thousands, to adequately train deep neural networks on various image analysis tasks. Due to availability of our limited dataset consisting of only 198 patients, features were extracted from DatSPECT images with four commonly used CNN architectures that were pre-trained on the ImageNet dataset. The ImageNet dataset consists of millions of natural images across 1,000 different class label categories. Several commonly used deep CNN-based architectures that were pre-trained on the ImageNet dataset, including VGG16, ResNet50, DenseNet121, and InceptionV3, were used to extract features from DatSPECT images from years 0 and 1. We hypothesized that these CNNs that were pre-trained on the natural image classification task with the ImageNet dataset should be able to extract generalized spatial features from DatSPECT images.

The maximum intensity projection (MIP) was first performed in the axial direction of the DatSPECT image slices (FIG. 4b). The MIPs obtained from the DatSPECT images from years 0 and 1 were used as input to the pre-trained VGG16, Resnet50, DenseNet121, and InceptionV3 CNN-based architectures. Imaging features were extracted from the last layer before the classification layer of each pre-trained network. These feature maps were input into a 2D global average pooling layer resulting in N-dimensional feature vectors containing information about the MIPs of DatSPECT images from years 0 and 1. The dimensionality of the feature vectors extracted from the VGG16, Resnet50, DenseNet121, and InceptionV3 networks were N=512, 2048, 1024, and 2048, respectively.

The feature vectors corresponding to the MIPs from years 0 and 1 were extracted from each pre-trained CNN-based architecture separately. The feature vectors from years 0 and 1 were treated as a time sequence consisting of two timepoints at years 0 and 1. This time sequence was then input into a LSTM-based network architecture to capture the temporal features between the MIPs of DatSPECT images from years 0 and 1 relevant for the prediction task. In addition, the feature vectors extracted from each pre-trained CNN architecture were also combined into one feature vector with a dimensionality of N=5632 (FIG. 4b) and was referred to as the All ImageNet feature vector. The All ImageNet feature vector from years 0 and 1 was also treated as a time sequence that was input into the LSTM-based network as well (FIG. 4b).

The relevant spatial features present in the DatSPECT images were first extracted using the pre-trained CNNs. Those spatial features extracted from DatSPECT imaging were then used as input to a LSTM network, which extracted the relevant temporal features (Hochreiter and Schmidhuber 1997). This differs from the previous method described in Example Section 2.2.1.1, where the relevant spatiotemporal features were extracted directly from the original DatSPECT images using a convolutional LSTM-based architecture in one step.

2.2.1.3 Image Feature Extraction Using Semi-Quantitative Imaging Measures

The semi quantitative imaging measures of SBR in the left caudate, right caudate, left putamen and right putamen were also used as predictors for the prediction task. Semi-quantitative imaging measures were input as a time sequence that consisted of two time points at years 0 and 1 to a LSTM network which extracted N-dimensional feature vectors corresponding to the relevant temporal features for the prediction task (FIG. 4c). As in Example Section 2.2.1.1, the dimensionality of the extracted feature vector was also N=64.

TABLE 1

The different sets of imaging feature combinations used as input to the approach as described in Example Section 2.2.3.

| | Feature Set Combinations |
|---|---|
| 1 | DatSPECT + Semi-quantitative + All ImageNet |
| 2 | DatSPECT + Semi-quantitative |
| 3 | DatSPECT + All ImageNet |
| 4 | Semi-quantitative + All ImageNet |
| 5 | DatSPECT Imaging Features |
| 6 | Semi-quantitative Imaging Features |
| 7 | All ImageNet Imaging Features |
| 8 | VGG16 Features |
| 9 | ResNet50 Features |
| 10 | DenseNet121 Features |
| 11 | InceptionV3 Features |

Note—DatSPECT imaging features refers to the imaging features extracted directly from the convolutional LSTM network architecture as described in Example Section 2.2.1.1. All ImageNet imaging features refers to the combined imaging features extracted from all four pre-trained CNN-based architectures of VGG16, ResNet50, DenseNet121, and InceptionV3 as described in Example Section 2.2.1.2. VGG16, ResNet50, DenseNet121, and InceptionV3 features refer to imaging features extracted from each pre-trained CNN architecture separately, as described in Example Section 2.2.1.2. Semi-quantitative refers to the SBR values from the right and left caudate and putamen as described in Example Section 2.2.1.3.

2.2.2 Stage 2: UPDRS-III Feature Extraction

In the second stage of the approach, a LSTM-based network was developed to take advantage of the time-dependent nature of the available longitudinal clinical data (FIG. 4d). The UPDRS-III information from years 0 and 1, as described in Example Section 2.1, were used as a time sequence input to the LSTM-based network. The LSTM-based network yielded N-dimensional feature vectors which capture the temporal features from the UPDRS-III sub-scores from years 0 and 1, where N=64.

2.2.3 Stage 3: Feature Aggregation and Ensemble-Based Prediction

The third stage combined the extracted features from DatSPECT images (Stage 1) and UPDRS-III sub-scores (Stage 2) via concatenation with other non-imaging clinical measure. Those combined features were input into a fully-connected layer predicted outcome at year 4 (FIG. 4e). Dropout with a drop probability of 0.5 was applied to the combined features to regularize the network (21). Multiple networks were trained with different sets of the extracted DatSPECT imaging features in Stage 1 generating 11 different models, as described in Example Section 2.2.1 (Table 1). The inputs to all models included both clinical measures and UPDRS-III information. All model predictions were aggregated in an ensemble and averaged to give the final predicted composite UPDRS-III score at year 4 (FIG. 4e).

2.3 Training and Hyperparameter Optimization for the Approach

The approach was trained using the training and validation sets by optimizing a mean absolute error loss function that quantified the error between the measured and predicted UPDRS-III scores in year 4. The network was optimized via a first-order gradient-based optimization algorithm, Adam.

A grid search was performed for hyperparameter optimization of the approach. The general range for each hyperparameter sweep spanned several orders of magnitude. The optimized hyperparameters included batch size, dropout probability, number of training epochs, the dimensionality of the N-dimensional feature vectors extracted from DatSPECT imaging (Stage 1) and the UPDRS-III sub-scores (Stage 2). Batch size is defined as the number of training examples used to update the network weights for each iteration of training. An epoch is defined as one pass over all the examples in the training set while training the network. The range of batch sizes tested was 4, 8, 16, 32, and 64. The range for dropout probability was 0, 0.3, 0.5 and 0.8. The range for number of training epochs was 75, 100, 150, 200, 250, 300, 500, and 1,000. The range for the dimensionality of the N-dimensional extracted feature vectors was N=4, 8, 16, 32, 64, 128, and 256.

TABLE 2

Optimized hyperparameters for the framework

| Hyperparameter | Value |
|---|---|
| Dimensionality of feature vectors (N) | 64 |
| Batch size | 32 |
| Training epochs | 200 |
| Dropout probability | 0.5 |

Hyperparameter optimization was performed by training the approach on the training set for each combination of hyperparameter values via grid search. The best performing combination of hypermeter values was considered to be the combination that yielded the smallest mean absolute error loss function value on the validation set. A detailed list of optimized hyperparameters are shown in Table 2. After the best set of hyperparameters was selected, the approach was trained on the data from the training and validation sets consisting of 158 patients using the optimized hyperparameters.

2.4 Evaluation of the Approach

The approach was evaluated on the test set of 40 patients on the outcome prediction task. The accuracy of the proposed approach was quantified by evaluating several standard evaluation metrics, including mean absolute error (MAE) (Willmott and Matsuura 2005), mean squared error (MSE) (Wang and Bovik 2009), relative error (RE) (Park and Stefanski 1998), Pearson's correlation coefficient (r), and Spearman's rank correlation coefficient ($r_S$) (Mukaka 2012).

The evaluation metrics of MAE, MSE, and RE quantify the error between the predicted and observed composite UPDRS-III scores in year 4 for the regression task and are defined as in equations (1), (2), and (3), respectively.

$$MAE = \frac{1}{N}\sum_{i=0}^{N}|\hat{y}_i - y_i| \quad (1)$$

$$MSE = \frac{1}{N}\sum_{i=0}^{N}(\hat{y}_i - y_i)^2 \quad (2)$$

$$RE = \frac{1}{N}\sum_{i=0}^{N}\left|\frac{\hat{y}_i - y_i}{y_i}\right| \quad (3)$$

The term $\hat{y}_i$ is defined as the predicted composite UPDRS-III score, the term is defined as the observed composite UPDRS-III score for the $i^{th}$ sample, and N is defined as the sample size. The vertical bars denote absolute value in equations (1) and (3). For metrics of MAE, MSE, and RE, lower values indicate more accurate prediction of the composite UPDRS-III score in year 4.

The Pearson's correlation coefficient measures the linear correlation between the predicted and observed composite UPDRS-III scores in year 4. The Spearman's correlation coefficient measures rank correlation between the predicted and observed composite UPDRS-III scores in year 4. Both correlation coefficients range from −1 to +1 where larger positive values indicate a larger positive correlation and vice versa for negative values. Higher values of the Pearson's and Spearman's correlation coefficient between the predicted and observed composite UPDRS-III scores in year 4 indicate more accurate prediction. According to Mukaka 2012, as a rule of thumb, correlation coefficient values greater than 0.7 indicate high positive correlation. The Pearson's and Spearman's correlation coefficients are defined in equations (4) and (5), respectively.

$$r = \frac{\text{cov}(\hat{y}_i, y_i)}{\sigma_{\hat{y}_i}\sigma_{y_i}} \quad (4)$$

$$r_s = \frac{\text{cov}(rg_{\hat{y}_i}, rg_{y_i})}{\sigma_{rg_{\hat{y}_i}}\sigma_{rg_{y_i}}} \quad (5)$$

For equations (4) and (5), cov is defined as covariance and σ is defined as the standard deviation. In equation (5), $rg_{\hat{y}_i}$ and $rg_{y_i}$ are defined as the rank variables for $\hat{y}_i$ and $y_i$, respectively (Mukaka 2012).

To further evaluate the performance of the approach, an ordinary least squares linear regression (Kilmer and Rodriguez 2017) was performed between the predicted and observed composite UPDRS-III scores in year 4. The ordinary least squares regression fit a linear model solving for the intercept ($\beta_1$) and slope ($\beta_2$) in equation (6) that best fits the relationship between the predicted and observed composite UPDRS-III scores.

$$\hat{y}_i = \beta_1 + \beta_2 y_i \quad (6)$$

The coefficient of determination or R value which indicates the goodness-of-fit of the regression (Prairie 1996) was reported as an evaluation metric for the proposed approach. The coefficient of determination indicates the amount of the total variance in the data that is explained by the fitted linear model. Values for $R^2$ range from 0 to 1 where higher values of $R^2$ indicate more accurate prediction of the composite UPDRS-III score in year 4. According to Starnes et al 2010, a $R^2$ value greater than 0.7 generally indicates a strong relationship between the observed data and the fitted values.

2.4.1 Varying the Input to the Approach

Given the availability of a heterogenous longitudinal dataset, the approach was compared to cases where the approach was given access to different aspects of the patient data. First, the ensemble-based approach is trained 11 times with all feature set combinations (Table 1) where the final output prediction is averaged across all 11 trained models. The performance of the ensemble-based approach is used as a baseline of comparison for four cases where the proposed approach is given different subsets of features of the patient data as given in Table 3.

TABLE 3

The different subsets of feature combinations used as input to the approach as described in Example Section 2.4.1

| | Feature Set Combinations |
|---|---|
| 1 | DatSPECT + UPDRS-III + Clinical Information |
| 2 | DatSPECT + UPDRS-III (No Clinical Information) |
| 3 | UPDRS-III + Clinical (No DatSPECT Information) |
| 4 | DatSPECT + Clinical (No UPDRS-III Information) |

Note—DatSPECT refers to the imaging features extracted directly from the convolutional LSTM network architecture using the procedure in Example Section 2.2.1.1. UPDRS-III refers to the non-imaging clinical features extracted from UPDRS-III sub-scores from years 0 and 1 using the procedure in Example Section 2.2.1.2. Clinical refers to the clinical measures of age, gender, and diagnosis duration with respect to time of diagnosis and time of appearance of symptoms.

In the first case, the approach is given information based on DatSPECT imaging in years 0 and 1, UPDRS-III sub-scores in years 0 and 1 and clinical measures, such as age, gender and diagnostic duration with respect to time of diagnosis and time of appearance of symptoms, as inputs. In the second case, the approach is given information based on DatSPECT imaging in years 0 and 1 and UPDRS-III sub-scores in years 0 and 1 (clinical measures are excluded) as inputs. In the third case, the approach is given information based on UPDRS-III sub-scores in years 0 and 1 and clinical measures (DatSPECT imaging information is excluded) as inputs. In the fourth case, the approach is given information based on DatSPECT imaging in years 0 and 1 and clinical measures (UPDRS-III sub-scores in years 0 and 1 are excluded) as inputs.

In all four cases, DatSPECT imaging features from years 0 and 1 were extracted using the method as described in Example Section 2.2.1.1. In each case, the network was only trained once on the input data (i.e. the final predicted composite UPDRS-III score in year 4 was given by the output of one trained model and not given by averaging the output an ensemble of multiple models).

In addition to evaluation on the basis of the standard evaluation metrics described in above in Example Section 2.4, the approach was compared to networks trained with a different subset of input features in each case by comparing the difference of squared errors between the ensemble-based approach and the networks trained for each case in Table 3. The difference of squared errors is given by equation (7).

$$MSE_{Diff,j} = \frac{1}{N}\sum_{i=0}^{N}(\hat{y}_{i,j} - y_i)^2 - (\hat{y}_{i,ensemble} - y_i)^2 \quad (7)$$

The term $\hat{y}_{i,j}$ is defined as the predicted composite UPDRS-III score in year 4 for the $i^{th}$ sample by the network trained using the feature subset combination for the $i^{th}$ case for j=1, . . . , 4 (Table 3). The term $\hat{y}_{i,ensemble}$ is defined as the predicted composite UPDRS-III score in year 4 for the $i^{th}$ sample by the ensemble-based approach. Positive (negative) values for the difference of squared errors indicate relatively worse (better) performance in each case when compared to the performance of the ensemble-based method. Lesser values indicate more accurate prediction of the composite UPDRS-III score in year 4 when compared to the ensemble-based approach.

2.4.2 Comparison of DatSPECT Image Feature Extraction Methods

The performance of the networks trained on the individual sets of extracted imaging features as described in Example Section 2.2.1 were also compared to the performance of the ensemble-based approach, which incorporated the predictions from all 11 trained networks. The approach was compared to 11 cases where different subsets of imaging features, as listed in Table 1, were given to the network as inputs. In all 11 cases, the network was also given clinical information and UPDRS-III sub-scores from years 0 and 1 as inputs. Similar to the procedure described in Example Section 2.4.1, in each case, the network was only trained once on the input data. Each case was evaluated using the evaluation metrics as in Example Section 2.4. The ensemble-based approach was also compared to networks trained with a different subset of input features in each case with the difference of squared errors given by equation (7) as described in Example Section 2.4.1.

2.5 Statistical Analysis and Implementation Details

Statistical significance was determined using a two-tailed t-test where a p<0.05 was used to infer a statistically significant difference. The network architecture and training were implemented in Python 3.6.8, TensorFlow 1.13.1, and Keras 2.2.5. Experiments were run on an NVIDIA Tesla K40 GPU and a Linux CentOS 7.8 operating system.

3. Results 3.1 Evaluating the Three-Stage CNN-RNN Ensemble-Based Approach

Figure 5:
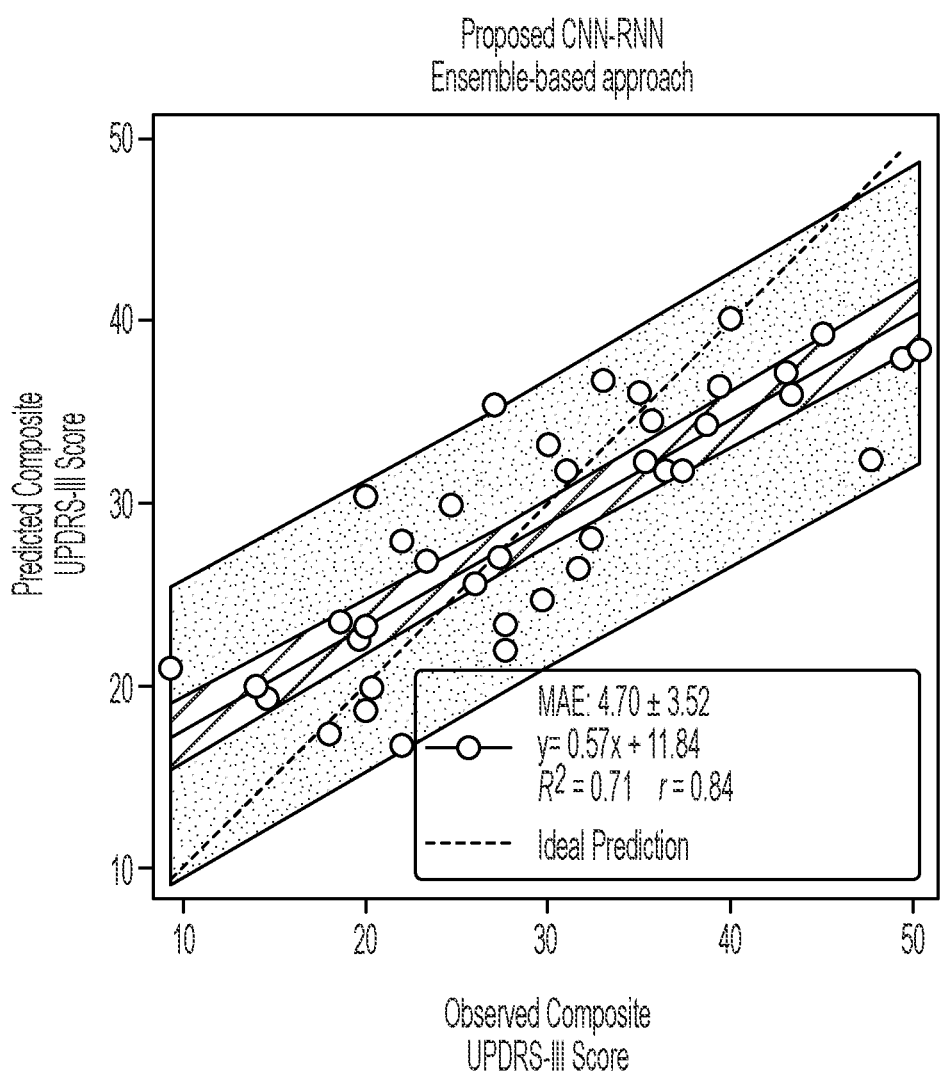
FIG. 5 is a scatter plot of the predicted vs observed composite UPDRS-III scores in year 4 by the ensemble-based approach on the test set. The black dashed line indicates perfect prediction of the observed composite UPDRS-III scores in year 4. The solid black line represents the ordinary least squares regression linear fit as described in Section 2.4. The hashed and remaining enclosed regions represent the 95% confidence and prediction intervals, respectively, for the regression line. The mean absolute error (MAE), Pearson's correlation coefficient (r), equation for the regression line, and $R^2$ value for the regression line are given in the legend.

The CNN-RNN ensemble-based approach yielded a MAE of 4.70 (95% confidence interval (CI): 3.77, 6.10), MSE of 37.18 (95% CI: 21.97, 52.40), and a RE of 0.18 (95% CI: 0.12, 0.25) between the predicted and observed composite UPDRS-III scores on the test set (FIG. 5 and Table 4). The ensemble-based approach also yielded a Pearson's and Spearman's correlation coefficient of 0.84 (p<0.001) and 0.86 (p<0.001), respectively, indicating a high positive correlation between the predicted and observed composite UPDRS-III scores (Table 4).

A scatter plot of the predicted versus observed composite UPDRS-III scores as predicted by the proposed ensemble-based approach on the test set is shown in FIG. 5. The regression line computed by ordinary least squares regression using the procedure in Example Section 2.4 is plotted as a solid black line overlaid on the scatter plot in FIG. 5. This was done to visualize the goodness-of-fit between the predicted and observed composite UPDRS-III values in year 4. The enclosed regions representing the 95% confidence interval and 95% prediction interval of the regression line, respectively, were also shown (FIG. 5). The $R^2$ value for the regression line for the proposed ensemble-based approach was 0.71, indicating a strong relationship between the predicted and observed UPDRS-III composite scores in year 4.

TABLE 4

Comparing the performance of the method when varying the features included in the input as described in Example Section 2.4.1

|  | Proposed Ensemble CNN-RNN-based Method | DatSPECT + UPDRS-III + Clinical Information | DatSPECT + UPDRS-III (No Clinical Information) | UPDRS-III + Clinical (No DatSPECT Information) | DatSPECT + Clinical (No UPDRS-III Information) |
|---|---|---|---|---|---|
| MAE | 4.70 | 5.04 | 5.22 | 6.63 | 9.15 |
|  | (3.56, 5.84) | (3.78, 6.29) | (4.09, 6.35) | (5.22, 8.14) | (6.90, 11.39) |
| MSE | 34.53 | 40.41 | 39.37 | 65.85 | 131.71 |
|  | (18.81, 50.25) | (22.09, 58.74) | (24.48, 54.25) | (36.14, 95.57) | (73.60, 189.81) |
| RE | 0.18 | 0.20 | 0.20 | 0.26 | 0.35 |
|  | (0.12, 0.25) | (0.12, 0.27) | (0.14, 0.26) | (0.18, 0.35) | (0.23, 0.48) |
| r | 0.84 | 0.81 | 0.81 | 0.64 | 0.04 |
|  | (p < 0.001) | (p < 0.001) | (p < 0.001) | (p < 0.001) | (n. s.) |
| $r_s$ | 0.86 | 0.82 | 0.84 | 0.73 | 0.03 |
|  | (p < 0.001) | (p < 0.001) | (p < 0.001) | (p < 0.001) | (n. s.) |
| $R^2$ | 0.71 | 0.66 | 0.66 | 0.41 | 0.00 |

Note—Data in parentheses are 95% confidence intervals. MAE: mean absolute error, MSE: mean squared error, n.s.: not significant, RE: relative error, r: Pearson correlation coefficient, $r_s$: Spearman's rank correlation coefficient, $R^2$: the coefficient of determination indicating the goodness-of-fit of the ordinary least squares regression performed between the predicted and observed UPDRS-III composite scores in year 4.

3.2 Evaluating the Approach when Varying the Input Features to the Network

Figure 6:
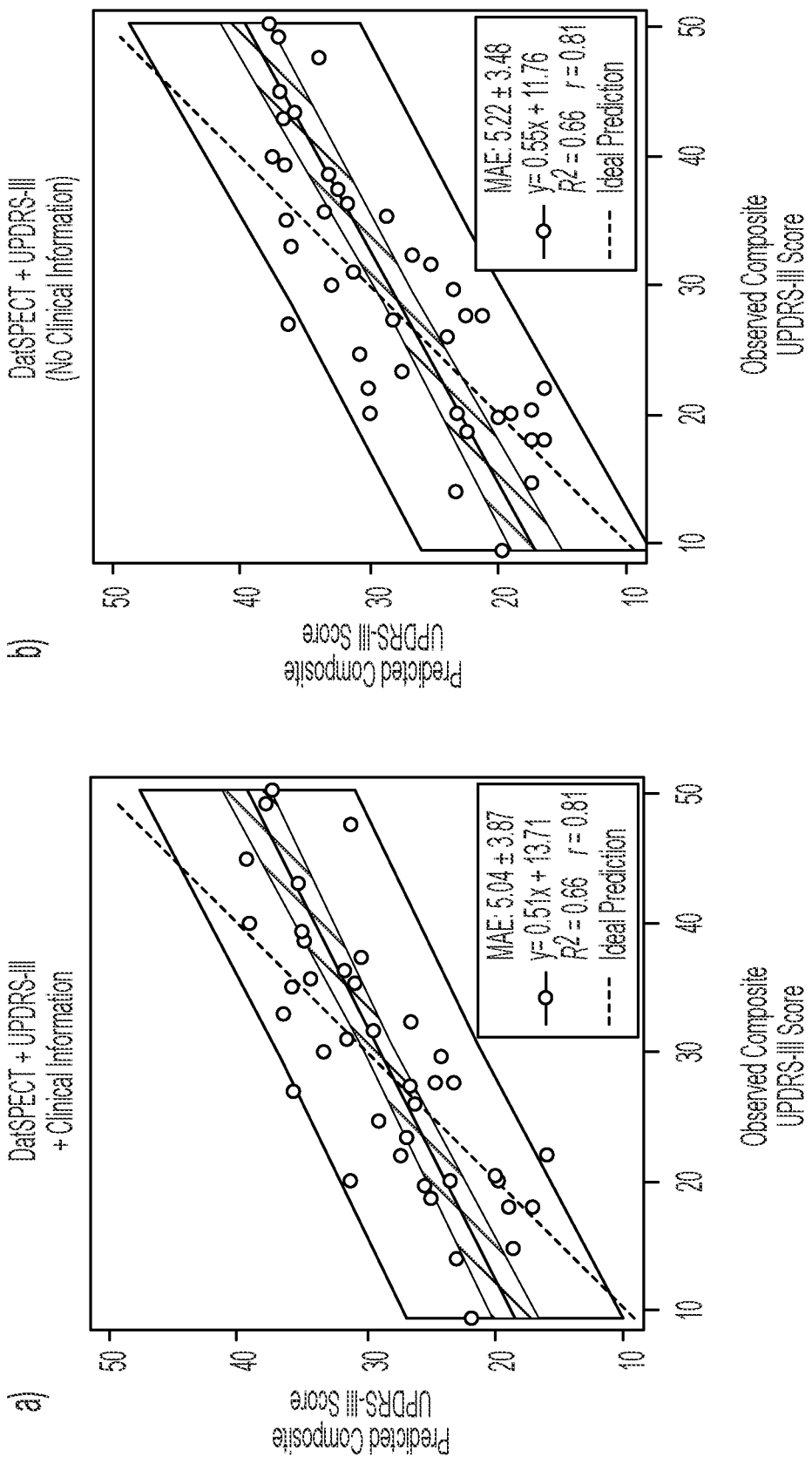
FIG. 6 (panels a-h) are scatter plots of the predicted vs observed composite UPDRS-III scores in year 4 on the test set by the networks trained with varying input feature combinations via the procedure in Example Section 2.4.1 (a-d). The black dashed line indicates perfect prediction of the observed composite UPDRS-III scores in year 4. The solid black lines represent the ordinary least squares regression linear fit as described in Example Section 2.4. The enclosed regions represent the 95% confidence and prediction intervals, respectively, for the regression line. The mean absolute error (MAE), Pearson's correlation coefficient (r), equation for the regression line, and $R^2$ value for the regression line for each case are given in the legend (a-d). The scatter plot and regression line of the ensemble-based approach is overlaid on the scatter plots for each case for direct comparison (e-h).
Figure 6:
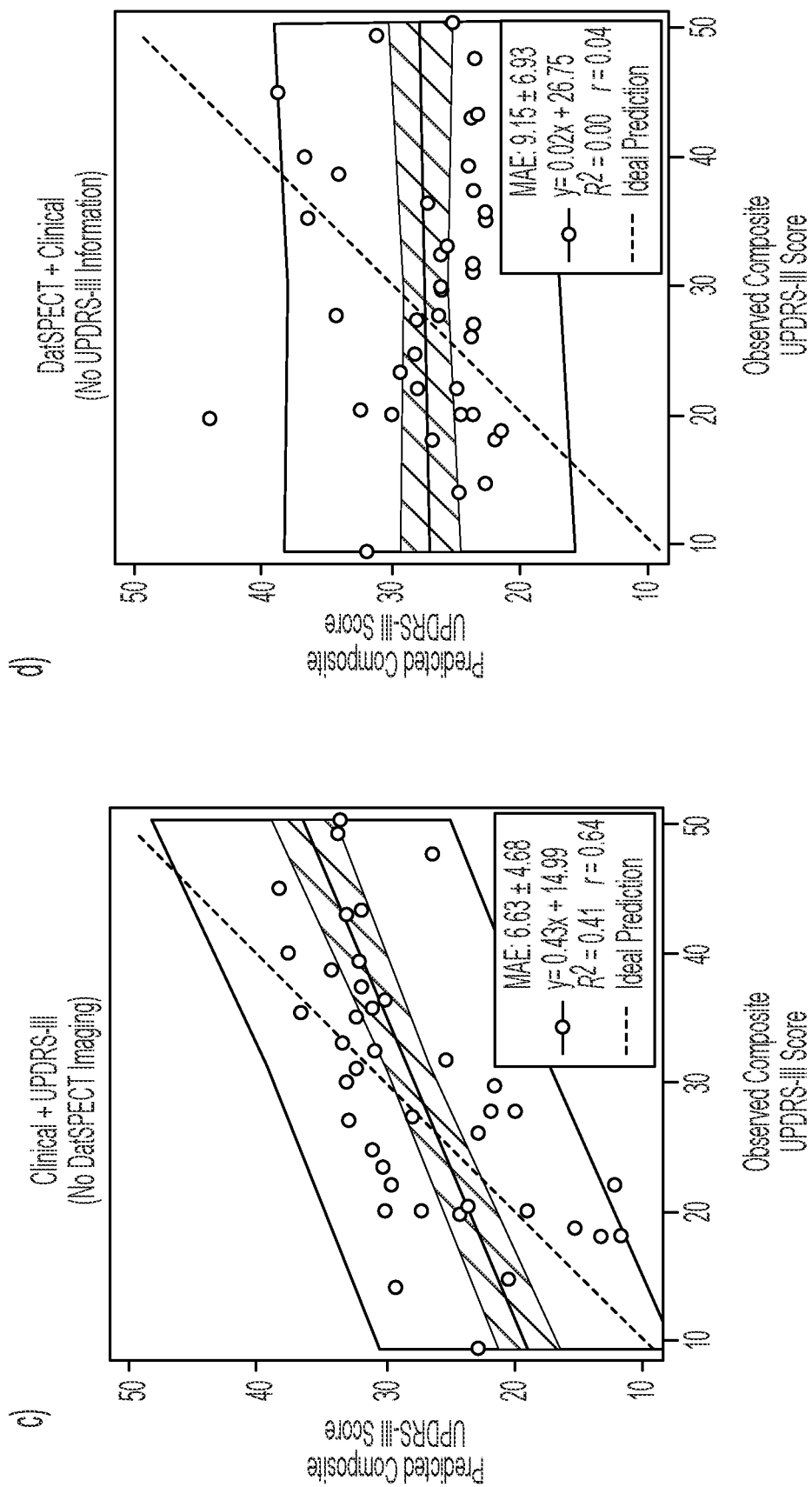
Figure 6:
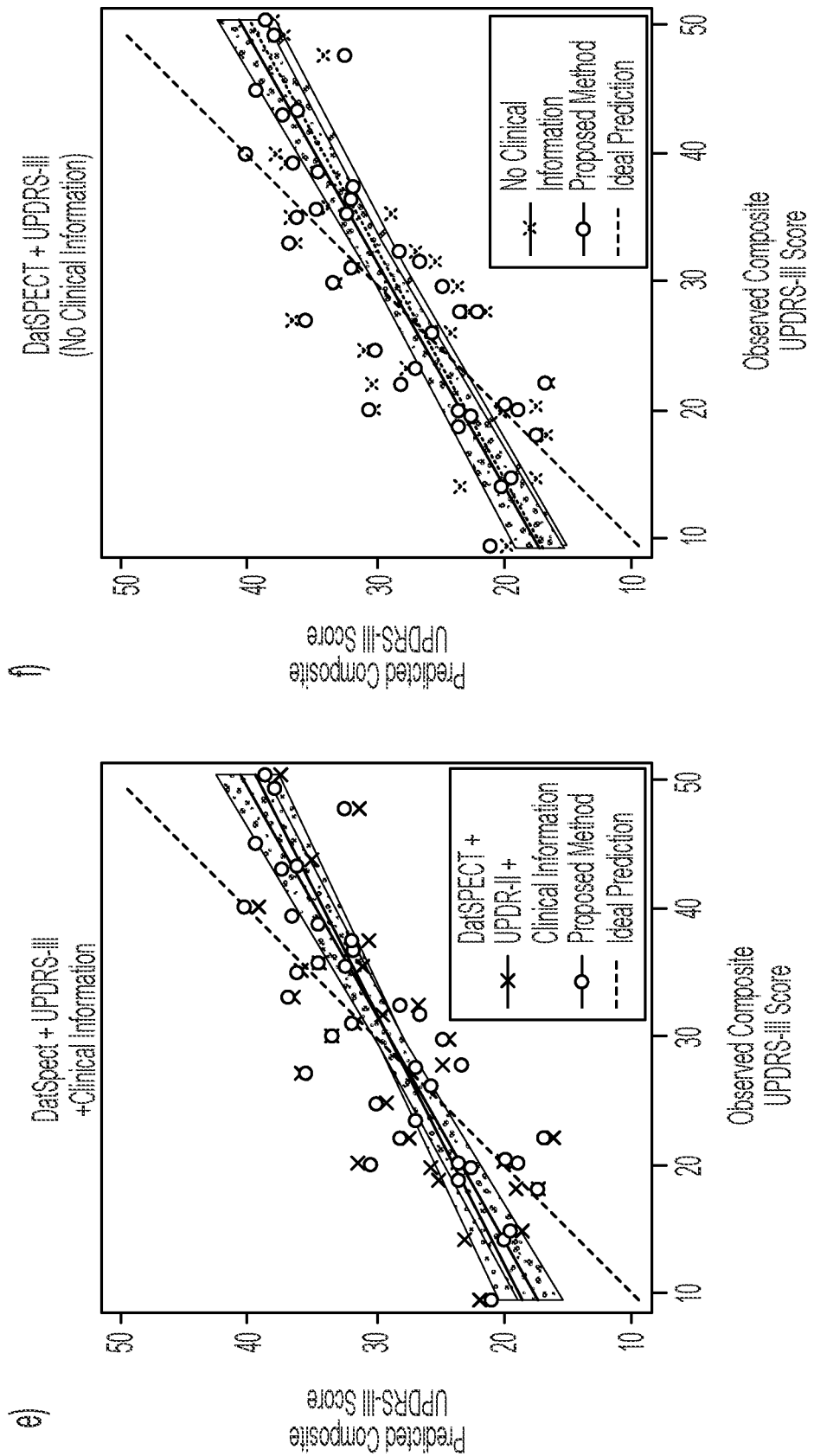
Figure 6:
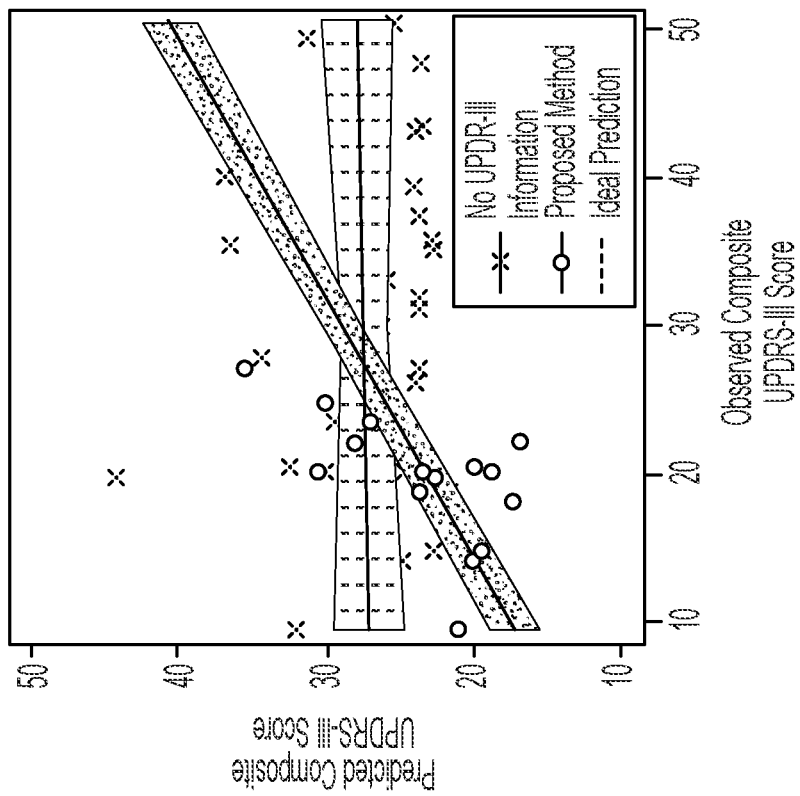
Figure 6:
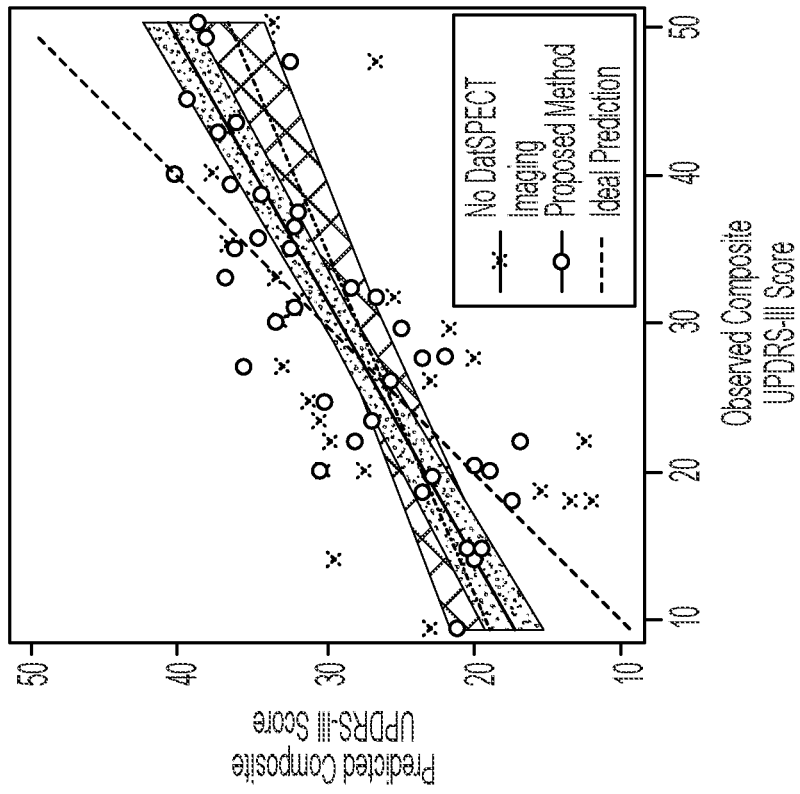

The performance of the networks trained with different subsets of input features as described in Example Section 2.4.1 were evaluated on the basis of standard evaluation metrics (Table 4) and compared to the ensemble-based approach that was trained with all the available input features (FIG. 6 The ensemble-based approach statistically outperformed the network trained with only input clinical measures and UPDRS-III information from years 0 and 1 (no DatSPECT imaging information) (FIGS. 6c and g), on the basis of MAE (p<0.05). The ensemble-based approach also statistically outperformed the network trained only with input DatSPECT imaging and clinical measures (no UPDRS-III information) (FIGS. 6d and h), on the basis of MAE, MSE and RE (p<0.05). The ensemble-based approach had the highest Pearson's correlation coefficient (0.84), Spearman's correlation coefficient (0.86), and $R^2$ value (0.71) when compared to the other networks that were given varying input feature sets (Table 4), indicating more accurate prediction of composite UPDRS-III scores in year 4.

The network trained with clinical inputs, DatSPECT and UPDRS-III information from years 0 and 1 and the network trained with only DatSPECT and UPDRS-III information (no input clinical measures) both statistically outperformed the network that was not given UPDRS-III information as inputs on the basis of MAE, MSE and RE (p<0.05) (Table 4). The two networks that were at least given DatSPECT and UPDRS-III information from years 0 and 1 as inputs both yielded Pearson's and Spearman's correlation coefficients greater than 0.80 (r, $r_s$>0.80) and an $R^2$ value of 0.66, indicating relatively high performance on the outcome prediction task.

Scatter plots of the predicted versus observed composite UPDRS-III scores as predicted by the networks trained with different subsets of input features are shown for each case in FIG. 6a-d. Regression lines computed by ordinary least squares regression using the procedure in Example Section 2.4 are also shown. The performance of the ensemble-based approach was directly compared to each case by overlaying the scatter plot of the predicted versus observed composite UPDRS-III scores in FIG. 6e-h.

Figure 7:
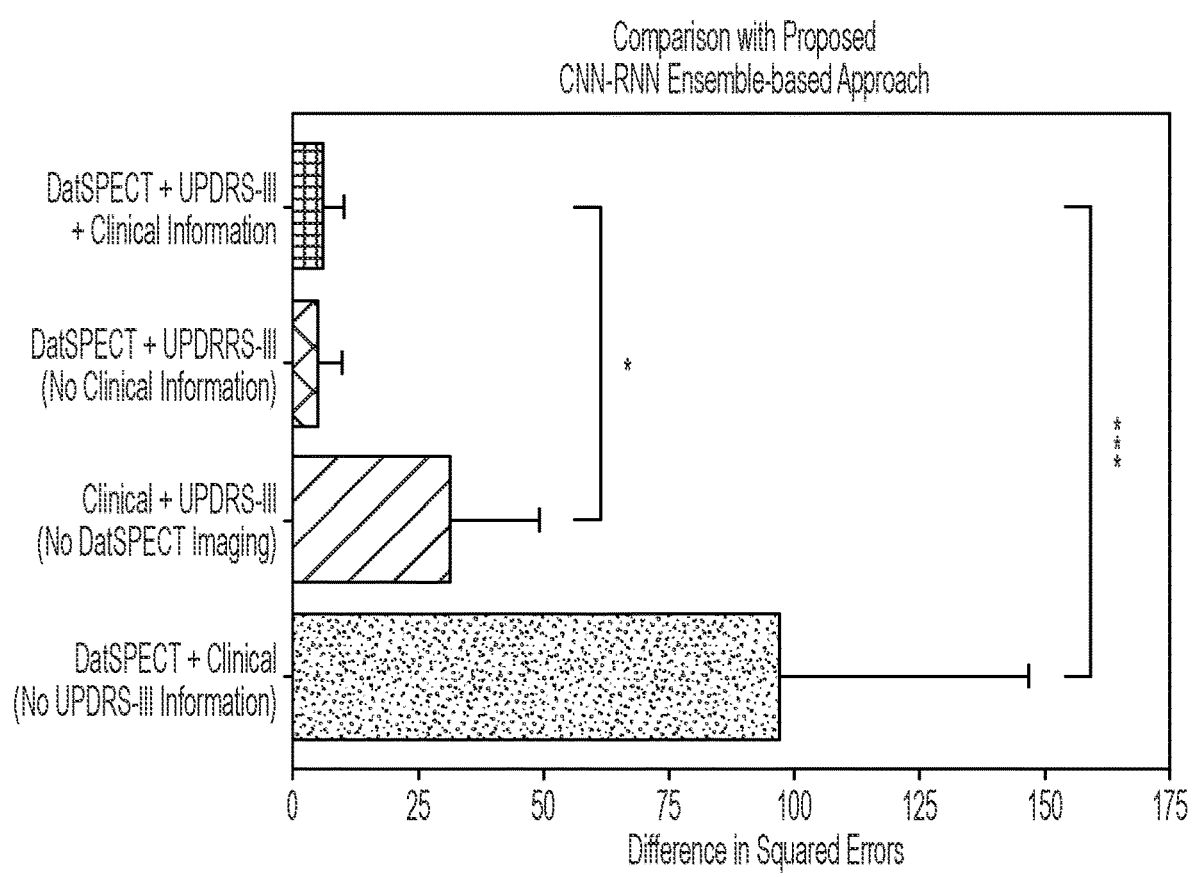
FIG. 7 is a plot showing a comparison of the networks that were given different subsets of input features to the ensemble-based approach by computing the difference in squared errors using the procedure in Example Section 2.4.1. Statistical significance is denoted by the * symbol where * is $p<0.05$,  is $p<0.005$ and * $p<0.0005$.

The performance of networks trained with different subsets of input features were compared to that of the ensemble-based method by computing the difference in squared errors using the procedure and equation (7) in Example Section 2.4.1 (FIG. 7). The network that was trained with clinical inputs, DatSPECT and UPDRS-III information from years 0 and 1 had a difference in squared errors of 5.89 (95% CI: 1.51, 10.27) and statistically outperformed the networks that were not given DatSPECT imaging information and UPDRS-III information from years 0 and 1 as inputs, respectively, on the basis of difference in squared errors (p<0.05) (FIG. 7). The network that was trained with DatSPECT and UPDRS-III information from years 0 and 1 (not given input clinical measures) also statistically outperformed the networks that were not given DatSPECT imaging information and UDPRS-III information from years 0 and 1 as inputs, respectively, on the basis of difference in squared errors (p<0.05) (FIG. 7).

3.3 Evaluating the Effectiveness Different Combinations of Extracted DatSPECT Imaging Features The performance of the ensemble-based approach was compared to that of 11 networks each trained with different subsets of input imaging features, which are listed in Table 1, as described in Example Section 2.4.2. The performance of these networks was evaluated on the basis of standard evaluation metrics (Table 5). The ensemble-based approach had the lowest MAE, MSE and RE compared to networks trained with different subsets of input imaging features (Table 5), indicating higher performance.

TABLE 5

Comparing the performance of the method when varying the source of DatSPECT imaging information to the input as described in Example Section 2.4.2

|  | MAE | MSE | RE | r | $r_s$ | $R^2$ |
| --- | --- | --- | --- | --- | --- | --- |
| Proposed Ensemble CNN-RNN-based Method | 4.70 (3.56, 5.84) | 34.53 (18.81, 50.25) | 0.18 (0.12, 0.25) | 0.84 (p < 0.001) | 0.86 (p < 0.001) | 0.71 |
| DatSPECT + Semi-quantitative + All ImageNet Features | 4.79 (3.65, 5.94) | 35.48 (20.11, 50.85) | 0.20 (0.12, 0.27) | 0.82 (p < 0.001) | 0.85 (p < 0.001) | 0.67 |
| DatSPECT + Semi-quantitative Imaging Features | 4.74 (3.36, 6.12) | 40.60 (14.59, 66.60) | 0.19 (0.11, 0.26) | 0.79 (p < 0.001) | 0.80 (p < 0.001) | 0.62 |
| DatSPECT + All ImageNet Imaging Features | 4.81 (3.45, 6.18) | 40.95 (19.94, 61.96) | 0.21 (0.12, 0.30) | 0.79 (p < 0.001) | 0.82 (p < 0.001) | 0.63 |
| Semi-quantitative + All ImageNet Imaging Features | 4.83 (3.69, 5.96) | 35.57 (20.41, 50.73) | 0.19 (0.13, 0.25) | 0.82 (p < 0.001) | 0.84 (p < 0.001) | 0.67 |
| DatSPECT Imaging Features | 5.04 (3.78, 6.29) | 40.41 (22.09, 58.74) | 0.20 (0.12, 0.27) | 0.81 (p < 0.001) | 0.82 (p < 0.001) | 0.66 |
| Semi-quantitative Imaging Features | 5.58 (4.13, 7.03) | 51.29 (27.25, 75.33) | 0.21 (0.14, 0.29) | 0.76 (p < 0.001) | 0.76 (p < 0.001) | 0.57 |
| All ImageNet Imaging Features | 5.15 (3.90, 6.40) | 41.44 (20.15, 62.72) | 0.20 (0.14, 0.27) | 0.78 (p < 0.001) | 0.83 (p < 0.001) | 0.62 |
| VGG16 Imaging Features | 5.54 (4.14, 6.94) | 49.31 (26.95, 71.67) | 0.22 (0.14, 0.29) | 0.75 (p < 0.001) | 0.79 (p < 0.001) | 0.56 |
| ResNet50 Imaging Features | 5.32 (4.03, 6.61) | 44.14 (25.64, 62.65) | 0.20 (0.14, 0.26) | 0.79 (p < 0.001) | 0.80 (p < 0.001) | 0.62 |
| DenseNet121 Imaging Features | 5.23 (3.90, 6.56) | 44.12 (23.23, 65.01) | 0.20 (0.13, 0.27) | 0.79 (p < 0.001) | 0.81 (p < 0.001) | 0.63 |
| InceptionV3 Imaging Features | 5.47 (4.17, 8.76) | 45.89 (25.32, 66.46) | 0.22 (0.14, 0.29) | 0.76 (p < 0.001) | 0.80 (p < 0.001) | 0.58 |

Note—Data in parentheses are 95% confidence intervals. MAE: mean absolute error, MSE: mean squared error, ns: not significant, RE: relative error, n Pearson correlation coefficient, $r_s$: Spearman's rank correlation coefficient, $R_2$: the coefficient of determination indicating the goodness-of-fit of the ordinary least squares regression performed between the predicted and observed UPDRS-III composite scores in year 4. Information about the clinical features and UPDRS-III scores in years 0 and 1 were given as input to the network in all cases.

Figure 8:
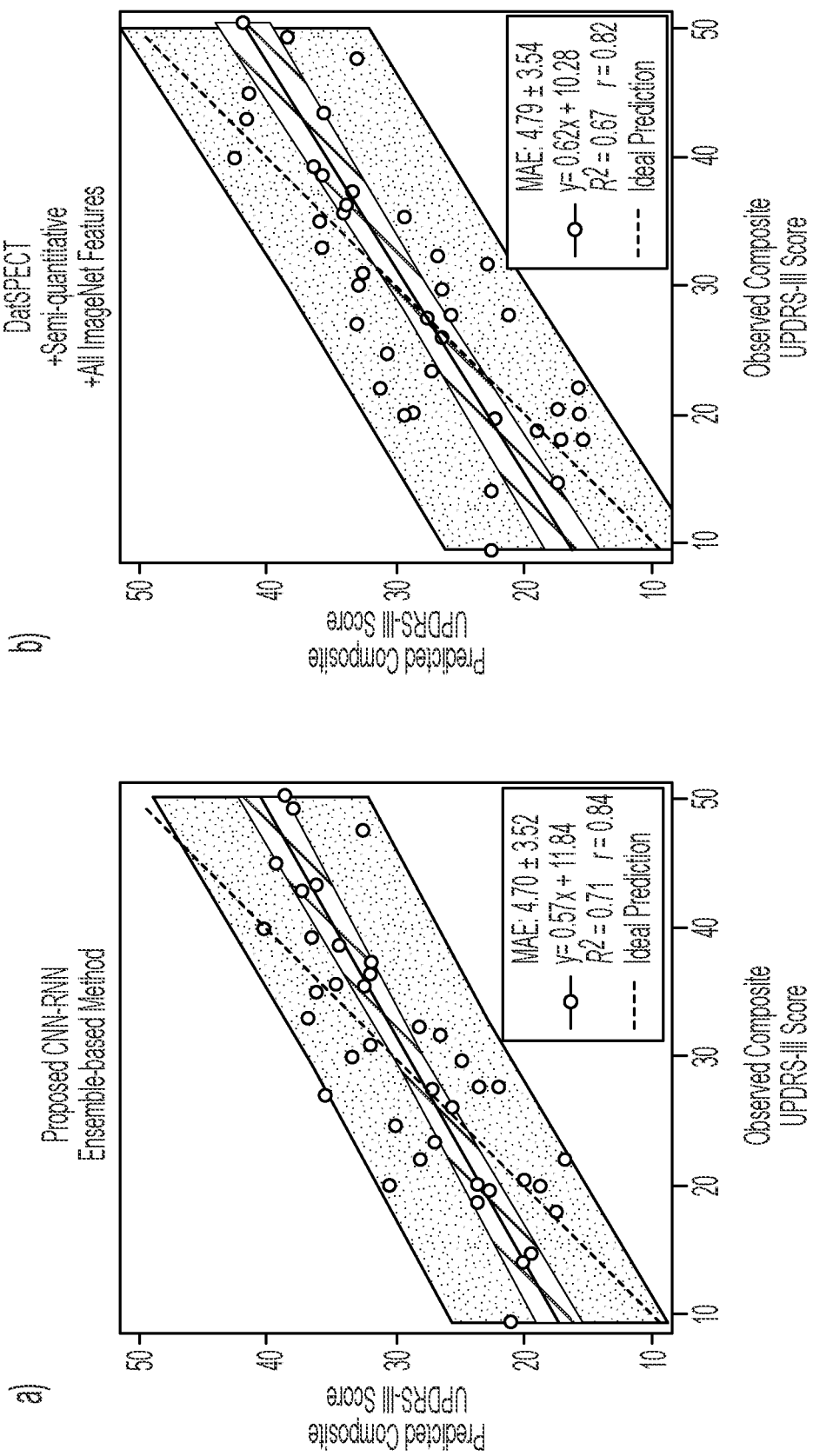
FIG. 8 (panels a-l) are scatter plots of the predicted vs observed composite UPDRS-III scores in year 4 on the test set by the networks trained with varying input imaging feature combinations given in Table 1 via the procedure in Example Section 2.4.2. In each case, the network was also given clinical information and UPDRS-III sub-scores from years 0 and 1 as inputs. The black dashed line indicates perfect prediction of the observed composite UPDRS-III scores in year 4. The solid black line represents the ordinary least squares regression linear fit as described in Example Section 2.4. The enclosed regions represent the 95% confidence and prediction intervals, respectively, for the regression line. The mean absolute error (MAE), Pearson's correlation coefficient (r), equation for the regression line, and $R^2$ value for the regression line for each case are given in the legend.
Figure 8:
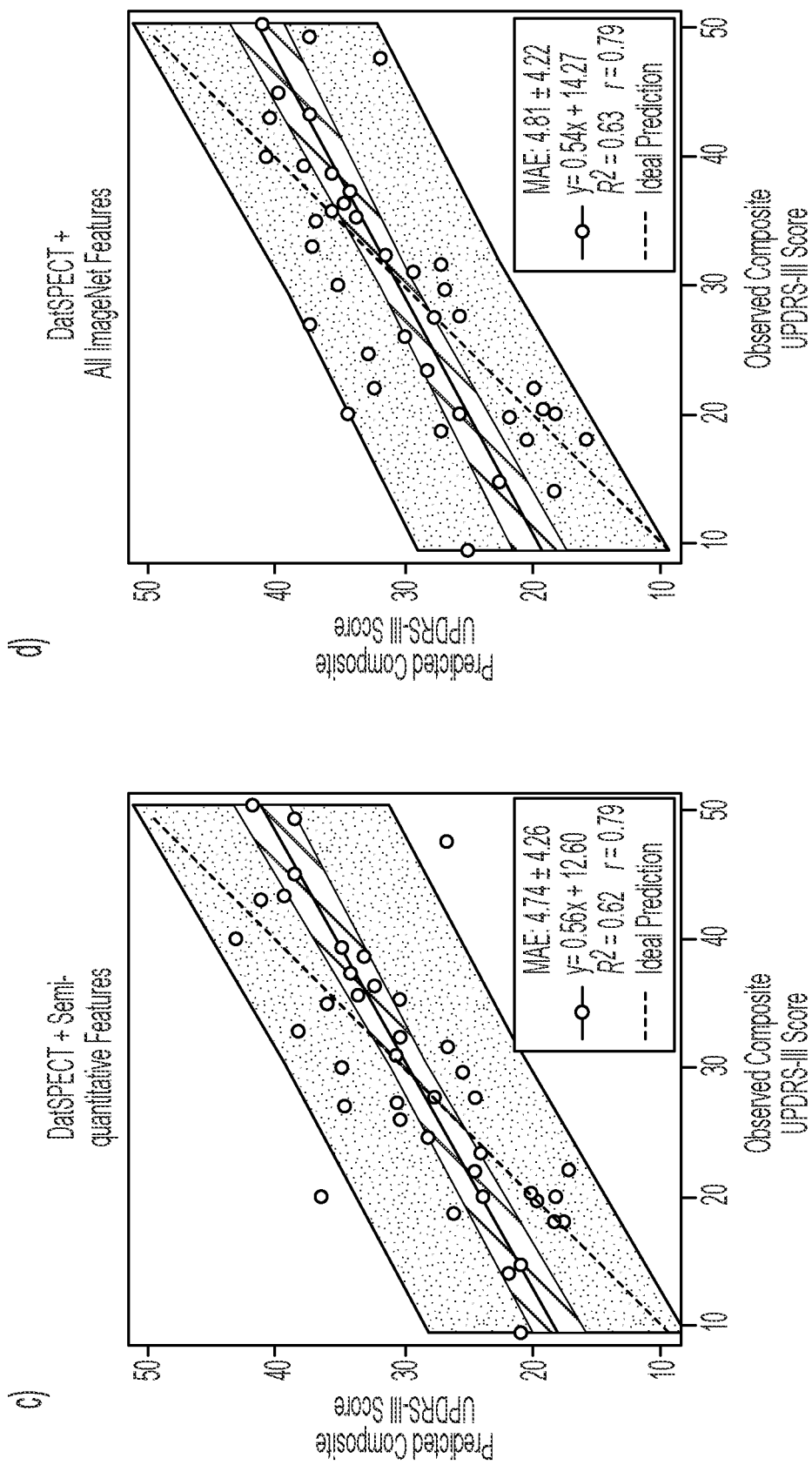
Figure 8:
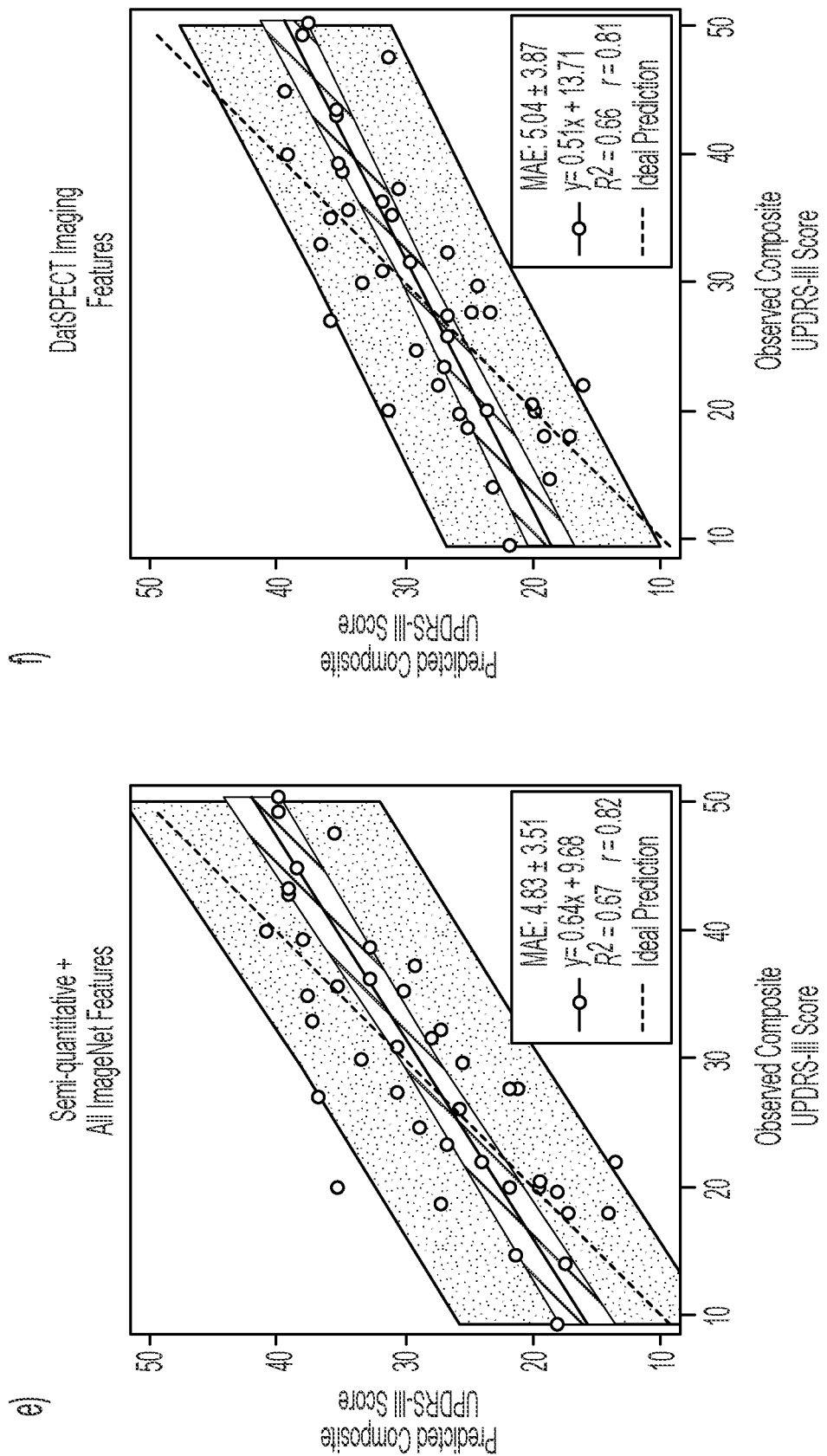
Figure 8:
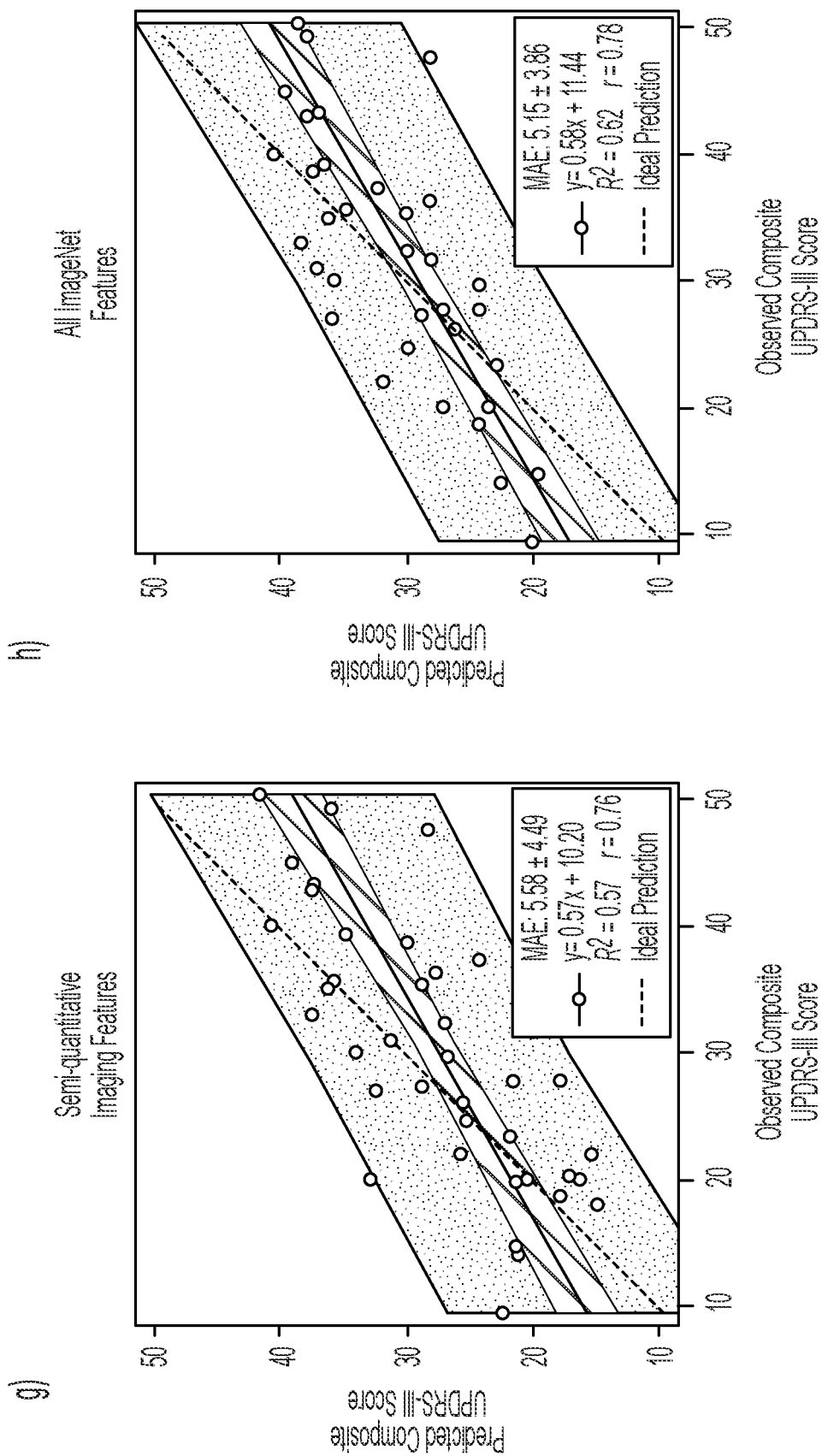
Figure 8:
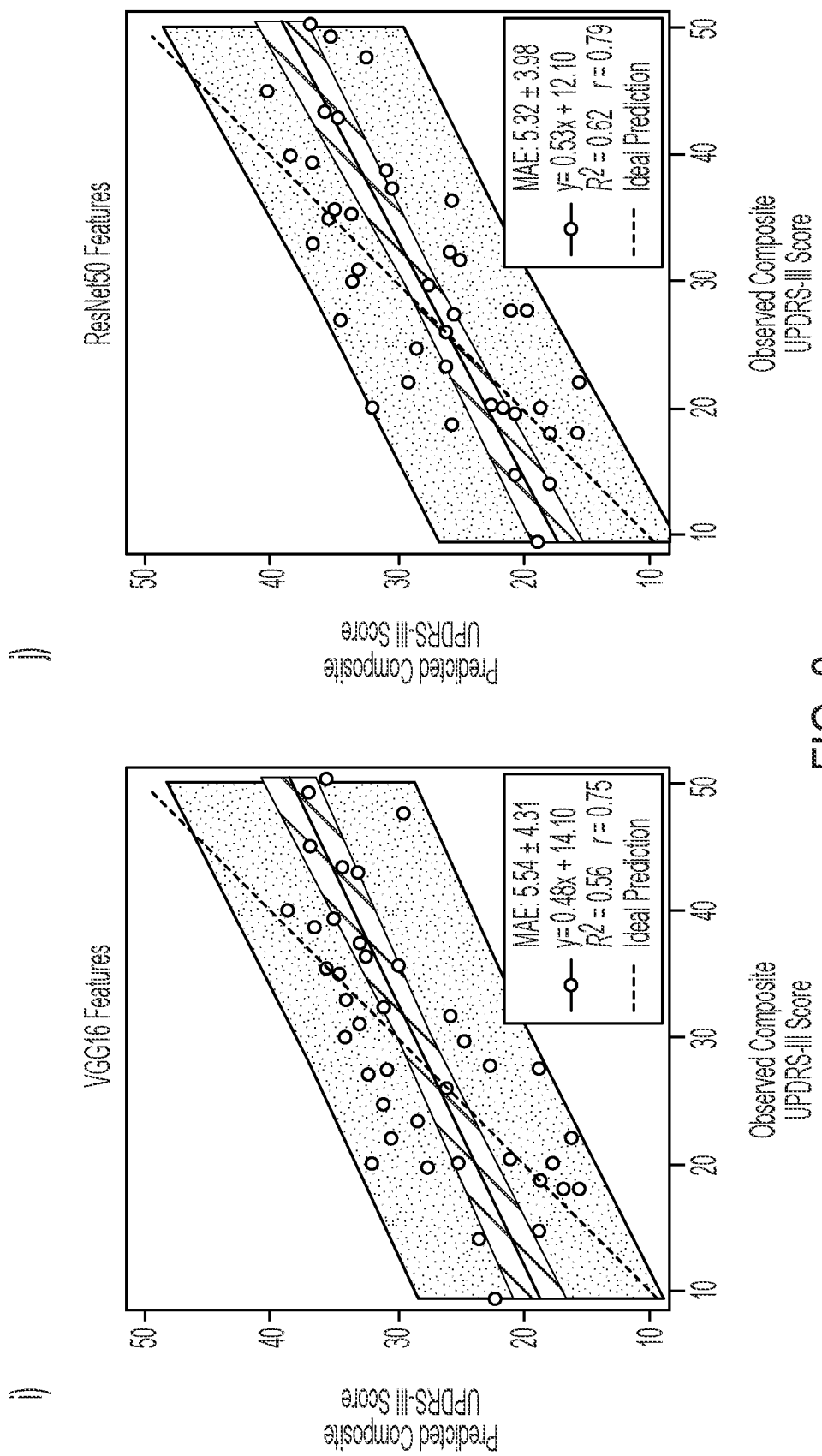
Figure 8:
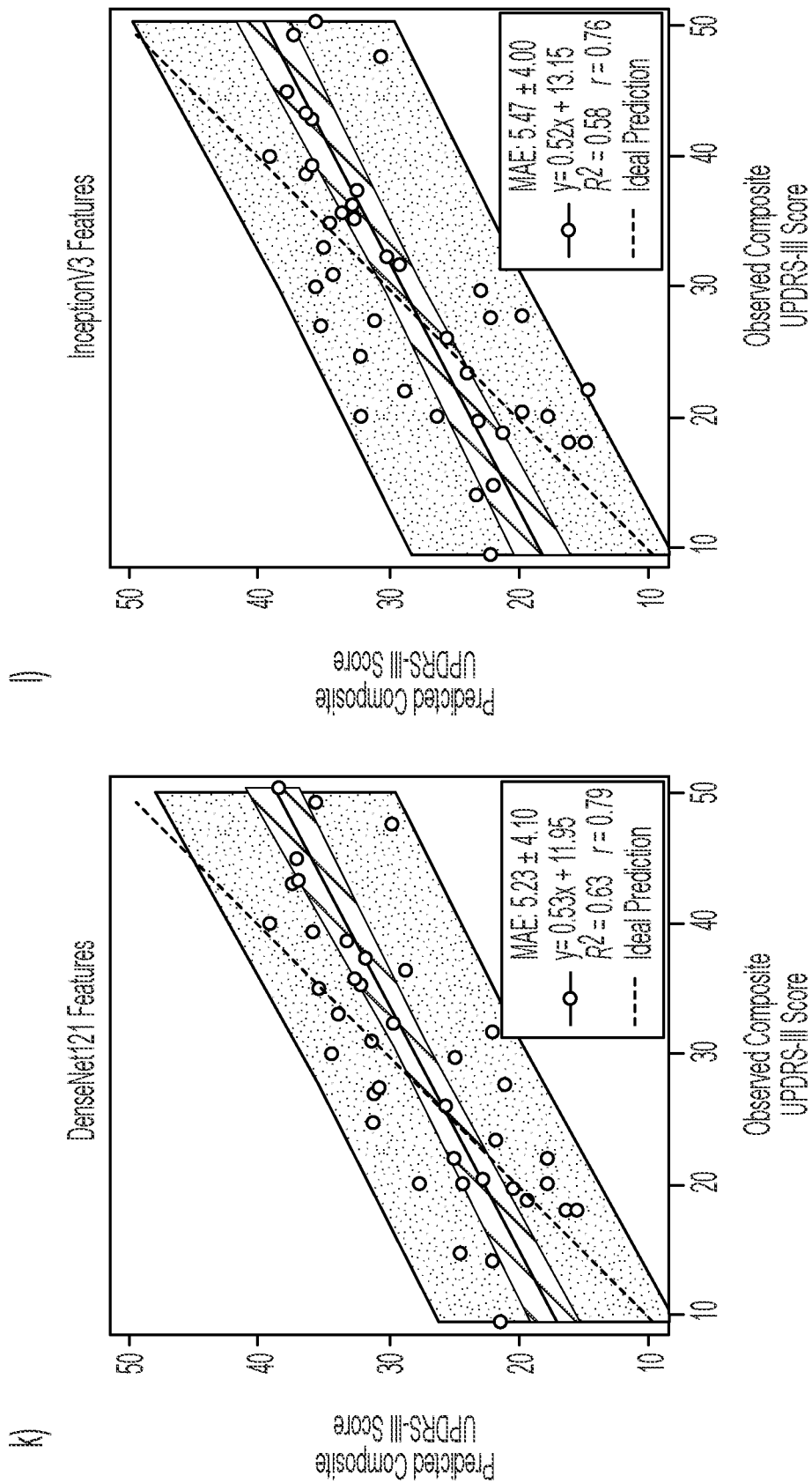

The ensemble-based approach also had the highest Pearson's correction coefficient, Spearman's correlation coefficients and $R^2$ value when compared to the other cases, indicating higher accuracy in prediction of composite UPDRS-III scores in year 4 (Table 5 and FIG. 8).

Figure 9:
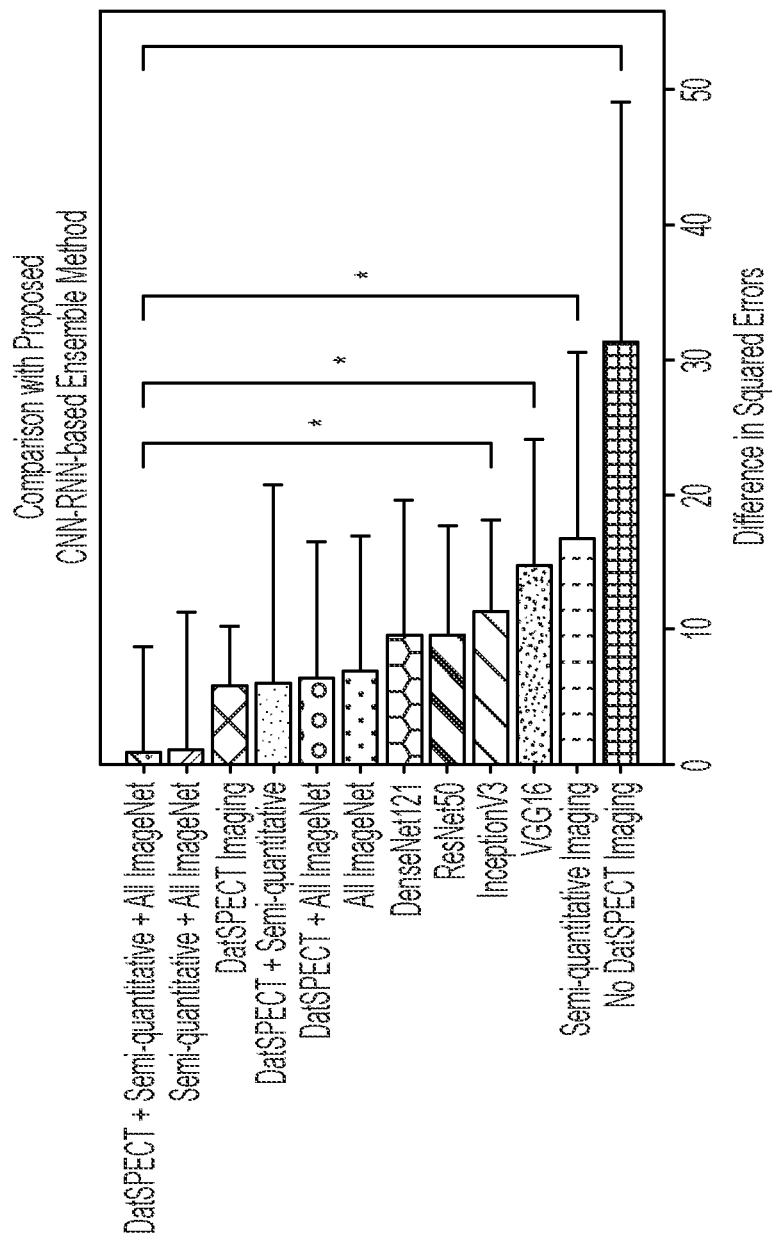
FIG. 9 is a plot showing a comparison of the networks that were given different subsets of input imaging features to the ensemble-based approach by computing the difference in squared errors using the procedure in Example Section 2.4.2. The case where the network is trained with no DatSPECT imaging information is also shown here for comparison. Statistical significance is denoted by the * symbol where * is $p<0.05$,  is $p<0.005$ and * is $p<0.0005$.

The performance of networks trained with 11 different subsets of input imaging features (Table 1) were compared to that of the ensemble-based method by computing the difference in squared errors (equation 7) using the procedure in Example Section 2.4.2 (FIG. 9). The network that was trained with imaging features derived from DatSPECT imaging, semi-quantitative imaging measures, and All ImageNet imaging features had the best relative performance and yielded a difference in squared errors of 0.95 (95% CI: −6.89, 8.80). That network also significantly outperformed the networks that were trained with only InceptionV3 features, VGG16 features, and semi-quantitative imaging features ($p<0.05$) on the basis of the difference in squared errors (FIG. 9).

4. Discussion

We developed a three-stage CNN-RNN deep learning ensemble-based approach for longitudinal outcome prediction of patients with Parkinson's disease. The ensemble-based approach took heterogenous longitudinal clinical data that consisted of both DatSPECT imaging and non-imaging clinical measures from years 0 and 1 as input and accurately predicted the composite UPDRS-III score in year 4 which was defined as outcome. In the first stage of the approach, spatiotemporal features were extracted from DatSPECT images from years 0 and 1. In this stage, convolutional LSTM-based architectures and CNN-based architectures pre-trained on ImageNet were used to extract the relevant DatSPECT imaging features. In the second stage, relevant temporal features were extracted from the UPDRS-III sub-scores from years 0 and 1. In the third stage, the extracted imaging and non-imaging features were combined with other clinical measures as inputs to train the proposed approach.

Multiple CNN-RNN architectures were trained on 11 different subsets of the extracted imaging features (Table 1) and their subsequent predictions were combined in an ensemble-learning based approach to yield the final predicted composite UPDRS-III scores in year 4. The ensemble-based approach had higher performance than that of the individual networks trained with different subsets of the extracted features (Table 4-5 and FIGS. 7 and 8) across several standard evaluation metrics, highlighting the clinical applicability of the ensemble-learning based framework.

The approach was also studied in the context of varying the training inputs to the network (FIG. 6). The networks that were not given DatSPECT imaging (FIG. 6c) and UPDRS-III sub-scores (FIG. 6d) from years 0 and 1 as inputs yielded a MAE of 6.63 and 9.15, respectively. The performance of those networks was significantly reduced ($p<0.05$), when compared to that of the network that received all the training inputs (FIG. 6a) which had a MAE of 5.04 (Table 4). In contrast, the network that was not given the clinical input measures for training (FIG. 6b) yielded a MAE of 5.22 which was not significantly different than that of the network that was given all of the available training inputs. This emphasizes the relative importance of the extracted DatSPECT imaging features and UPDRS-III non-imaging features for the outcome prediction task. While this suggests that information about the UPDRS-III sub-scores from years 0 and 1 were most important for the prediction task, the DatSPECT imaging features also contributed significantly to the performance of the proposed approach.

The importance of the extracted DatSPECT imaging features for the prediction task is further highlighted in FIG. 9. The network that received information about imaging measures from the original DatSPECT images, semi-quantitative imaging measures and the imaging features extracted from the CNN-based architectures pre-trained on the ImageNet dataset had the highest relative performance on the basis of the difference of squared errors. Interestingly, networks that received at least two or more sources of DatSPECT imaging input features tended to do better than those that received only one source of extracted input imaging features (FIG. 9). In fact, the top three performers were networks that were given some combination of the original DatSPECT images, semi-quantitative imaging measures, and All ImageNet features (Table 5). This suggests that complementary information relevant for the prediction task was extracted from the different sources of DatSPECT imaging information. The networks that received at least one source of DatSPECT imaging input features, with the exception of the networks trained only on VGG16 features or semi-quantitative imaging features, respectively, significantly outperformed the network that was not given any DatSPECT imaging features as input ($p<0.05$), which further emphasizes the importance of imaging for the prediction task (FIG. 9).

The ensemble-based approach leverages of the availability of a heterogenous dataset and trains multiple CNN-RNN architectures to focus on different aspects of the input data. The ensemble of predictions made by the network architectures trained on different aspects of the data improved the predictive power of the approach. The approach can be trained in an end-to-end parallelized fashion, where each network comprising the ensemble is trained in parallel. However, larger computational resources are required compared training a single model which may limit the utility of the approach in a clinical setting where such resources are not available. The performance of the single network that was trained on all the available imaging features was similar to that of the ensemble-based approach and may be acceptable for use in such cases. (FIGS. 8a-b and 9).

The approach employed ensemble averaging where the outputs of across all models were averaged to yield the final predicted outcome score and showed improved performance over individual models. Notably, one study developed an meta-learner method for cancer detection based on stacked generalization where the output of several machine learning classifiers were used as inputs into a neural network that performed the final classification (Xiao et al 2018). Integrating the proposed approach in such a meta-learner scheme could further improve performance and is an important area of research.

5. Conclusion

A three-stage CNN-RNN ensemble-based deep learning approach was developed for longitudinal outcome prediction of patients with PD and provided accurate prediction of motor outcome in year 4. The proposed approach provided several methods for extracting the relevant spatiotemporal imaging features from DatSPECT images and demonstrated the importance of combining imaging and non-imaging features for the outcome prediction task. Variants incorporate the approach disclosed herein into a prognostic tool that further characterize patients with PD into different groups based on disease progression. This prognostic tool aides in selecting appropriate treatments or therapy regimens for each patient to reduce symptoms and ultimately delay disease progression.

While the foregoing disclosure has been described in some detail by way of illustration and example for purposes of clarity and understanding, it will be clear to one of ordinary skill in the art from a reading of this disclosure that various changes in form and detail can be made without departing from the true scope of the disclosure and may be practiced within the scope of the appended claims. For example, all the methods, devices, systems, computer readable media, and/or component parts or other aspects thereof can be used in various combinations. All patents, patent applications, websites, other publications or documents, and the like cited herein are incorporated by reference in their entirety for all purposes to the same extent as if each individual item were specifically and individually indicated to be so incorporated by reference.

What is claimed is:

1. A method of generating a model to predict prospective pathology scores of test subjects having a pathology, the method comprising:
    extracting a first plurality of image features directly from sets of longitudinal single photon emission computed tomography (SPECT) and/or positron emission tomography (PET) images obtained from a plurality of reference subjects having the pathology, wherein the image features extracted from at least first and second sets of the longitudinal SPECT and/or PET images are extracted separate from one another to produce a first feature vector;
    extracting a second plurality of image features from maximum intensity projections (MIPs) of the sets of the longitudinal SPECT and/or PET images to produce a second feature vector;
    extracting a third plurality of image features from semi-quantitative imaging measures of the sets of the longitudinal SPECT and/or PET images to produce a third feature vector;
    extracting a plurality of non-imaging features from non-imaging data obtained from the plurality of reference subjects having the pathology to produce a fourth feature vector; and,
    training multiple artificial neural networks (ANNs) using the first, second, third, and fourth feature vectors and a plurality of clinical features from clinical data obtained from the plurality of reference subjects having the pathology to produce an ensemble of ANNs, thereby generating the model to predict prospective pathology scores of test subjects having the pathology.

2. The method of claim 1, wherein the ensemble of ANNs comprises at least one convolutional neural network (CNN) and at least one recurrent neural network (RNN).

3. The method of claim 1, wherein the ANN is not further trained on a classification task.

4. The method of claim 1, wherein the ANN comprises one or more recurrent neural networks (RNNs).

5. The method of claim 4, wherein the RNNs comprise one or more long short-term memory (LSTM) networks and/or one or more gated recurrent units (GRUs).

6. The method of claim 1, further comprising extracting the second plurality of images features using one or more pre-trained convolutional neural networks (CNNs).

7. A method of generating a model to predict prospective pathology scores of test subjects having a pathology, the method comprising:
    extracting a first plurality of image features from sets of longitudinal single photon emission computed tomography (SPECT) and/or positron emission tomography (PET) images obtained from a plurality of reference subjects having the pathology, wherein the images features extracted from at least first and second sets of the longitudinal SPECT and/or PET images are extracted separate from one another to produce a first feature vector;
    extracting a second plurality of image features from the sets of the longitudinal SPECT and/or PET images when the longitudinal SPECT and/or PET images are in an unprocessed form to produce a second feature vector;
    extracting a plurality of clinical features from clinical data obtained from the plurality of reference subjects having the pathology, which clinical features comprise pathology sub-scores to produce a third feature vector; and,
    training one or more layers of an artificial neural network (ANN) using the first, second, and third feature vectors, thereby generating the model to predict prospective pathology scores of test subjects having the pathology.

8. The method of claim 7, wherein the ensemble of ANNs comprises at least one convolutional neural network (CNN) and at least one recurrent neural network (RNN).

9. The method of claim 7, wherein the ANN is not further trained on a classification task.

10. The method of claim 7, wherein the ANN comprises one or more recurrent neural networks (RNNs).

11. The method of claim 10, wherein the RNNs comprise one or more long short-term memory (LSTM) networks and/or one or more gated recurrent units (GRUs).

12. The method of claim 7, further comprising extracting the second plurality of images features using one or more pre-trained convolutional neural networks (CNNs).

13. A system, comprising at least one controller that comprises, or is capable of accessing, computer readable media comprising non-transitory computer executable instructions which, when executed by at least one electronic processor, perform at least:
    extracting a first plurality of image features directly from sets of longitudinal single photon emission computed tomography (SPECT) and/or positron emission tomography (PET) images obtained from a plurality of reference subjects having the pathology, wherein the images features extracted from at least first and second sets of the longitudinal SPECT and/or PET images are extracted separately from one another to produce a first feature vector;
    extracting a second plurality of image features from maximum intensity projections (MIPs) of the sets of the longitudinal SPECT and/or PET images to produce a second feature vector;
    extracting a third plurality of image features from semi-quantitative imaging measures of the sets of the longitudinal SPECT and/or PET images to produce a third feature vector;
    extracting a plurality of non-imaging features from non-imaging data obtained from the plurality of reference subjects having the pathology to produce a fourth feature vector;
    training multiple artificial neural networks (ANNs) using the first, second, third, and fourth feature vectors and a plurality of clinical features from clinical data obtained from the plurality of reference subjects having the pathology to produce an ensemble of ANNs; and, using the ensemble of ANNs to predict a prospective pathology score of a test subject having the pathology.

14. A system, comprising at least one controller that comprises, or is capable of accessing, computer readable media comprising non-transitory computer executable instructions which, when executed by at least one electronic processor, perform at least:
- extracting a first plurality of image features from sets of longitudinal single photon emission computed tomography (SPECT) and/or positron emission tomography (PET) images obtained from a plurality of reference subjects having the pathology, wherein the image features extracted from at least first and second sets of the longitudinal SPECT and/or PET images are extracted separately from one another to produce a first feature vector;
- extracting a second plurality of image features from the sets of the longitudinal SPECT and/or PET images when the longitudinal SPECT and/or PET images are in an unprocessed form to produce a second feature vector;
- extracting a plurality of clinical features from clinical data obtained from the plurality of reference subjects having the pathology, which clinical features comprise pathology sub-scores to produce a third feature vector;
- training one or more layers of an artificial neural network (ANN) using the first, second, and third feature vectors to generate a predictive model; and,
- using the predictive model to predict a prospective pathology score of a test subject having the pathology.

15. A computer readable media comprising non-transitory computer executable instruction which, when executed by at least electronic processor perform at least:
- extracting a first plurality of image features directly from sets of longitudinal single photon emission computed tomography (SPECT) and/or positron emission tomography (PET) images obtained from a plurality of reference subjects having the pathology, wherein the images features extracted from at least first and second sets of the longitudinal SPECT and/or PET images are extracted separate from one another to produce a first feature vector;
- extracting a second plurality of image features from maximum intensity projections (MIPs) of the sets of the longitudinal SPECT and/or PET images to produce a second feature vector;
- extracting a third plurality of image features from semi-quantitative imaging measures of the sets of the longitudinal SPECT and/or PET images to produce a third feature vector;
- extracting a plurality of non-imaging features from non-imaging data obtained from the plurality of reference subjects having the pathology to produce a fourth feature vector;
- training multiple artificial neural networks (ANNs) using the first, second, third, and fourth feature vectors and a plurality of clinical features from clinical data obtained from the plurality of reference subjects having the pathology to produce an ensemble of ANNs; and,
- using the ensemble of ANNs to predict a prospective pathology score of a test subject having the pathology.

16. A computer readable media comprising non-transitory computer executable instruction which, when executed by at least electronic processor perform at least:
- extracting a first plurality of image features from sets of longitudinal single photon emission computed tomography (SPECT) and/or positron emission tomography (PET) images obtained from a plurality of reference subjects having the pathology, wherein the images features extracted from at least first and second sets of the longitudinal SPECT and/or PET images are extracted separately from one another to produce a first feature vector;
- extracting a second plurality of image features from the sets of the longitudinal SPECT and/or PET images when the longitudinal SPECT and/or PET images are in an unprocessed form to produce a second feature vector;
- extracting a plurality of clinical features from clinical data obtained from the plurality of reference subjects having the pathology, which clinical features comprise pathology sub-scores to produce a third feature vector;
- training one or more layers of an artificial neural network (ANN) using the first, second, and third feature vectors to generate a predictive model; and,
- using the predictive model to predict a prospective pathology score of a test subject having the pathology.

* * * * *